United States Patent
Tojo et al.

(12) 
(10) Patent No.: US 6,346,638 B1
(45) Date of Patent: Feb. 12, 2002

(54) PROCESS FOR CONTINUOUS PRODUCTION OF DIALKYL CARBONATE AND DIOL

(75) Inventors: Masahiro Tojo; Kazuhiro Oonishi, both of Kurashiki (JP)

(73) Assignee: Asahi Kasel Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/674,769

(22) PCT Filed: Jun. 10, 1999

(86) PCT No.: PCT/JP99/03092

§ 371 Date: Nov. 6, 2000

§ 102(e) Date: Nov. 6, 2000

(87) PCT Pub. No.: WO99/64382

PCT Pub. Date: Dec. 16, 1999

(30) Foreign Application Priority Data

Jun. 10, 1998 (JP) .......................................... 10-162423

(51) Int. Cl.⁷ .......................... C07C 68/06; C07C 69/96
(52) U.S. Cl. ........................................ 558/277; 558/275
(58) Field of Search .................................. 558/277, 275

(56) References Cited

U.S. PATENT DOCUMENTS

| | | | | |
|---|---|---|---|---|
| 4,181,676 A | * | 1/1980 | Buysch et al. ............... | 260/463 |
| 4,307,032 A | * | 12/1981 | Krimm et al. ............... | 260/463 |
| 4,506,086 A | * | 3/1985 | Salzburg et al. ............. | 549/464 |
| 4,661,609 A | | 4/1987 | Knifton | |
| 5,359,118 A | | 10/1994 | Wagner et al. | |
| 5,847,189 A | | 12/1998 | Tojo et al. | |

FOREIGN PATENT DOCUMENTS

| | | |
|---|---|---|
| JP | A4198141 | 7/1992 |
| JP | A977706 | 3/1997 |
| JP | 09176061 | 8/1997 |
| JP | A9278689 | 10/1997 |
| JP | A1036297 | 2/1998 |

* cited by examiner

Primary Examiner—Floyd D. Higel
Assistant Examiner—Kamal Saeed
(74) Attorney, Agent, or Firm—Birch, Stewart, Kolasch & Birch, LLP

(57) ABSTRACT

A method for continuously producing a (A) dialkyl carbonate and a (B) diol, comprising continuously feeding a cyclic carbonate and an aliphatic monohydric alcohol to a continuous multi-stage distillation column to thereby effect a transesterification therebetween, thereby continuously producing a dialkyl carbonate and a diol, while continuously withdrawing a low boiling point mixture containing the produced dialkyl carbonate (A) in a gaseous form from an upper portion of the distillation column and continuously withdrawing a high boiling point mixture containing the produced diol (B) in a liquid form from a lower portion of the distillation column, wherein the transesterification is performed under conditions wherein: (a) the reaction pressure of the column bottom is $5 \times 10^4$ Pa or less; (b) the reaction temperature of the column bottom is in the range of from $-20°$ C. to less than $60°$ C.; and (c) the distillation column has an F-factor in the range of from 0.2 to 5.0, the F-factor being represented by the following formula (1):

$$F\text{-factor} = u_g(\rho_g)^{1/2} \quad (1)$$

wherein $u_g$ represents the gas velocity (m/s) in the distillation column and $\rho_g$ represents the gas density (kg/m³) in the distillation column.

6 Claims, 1 Drawing Sheet

US 6,346,638 B1

PROCESS FOR CONTINUOUS PRODUCTION OF DIALKYL CARBONATE AND DIOL

This application is the national phase under 35 U.S.C. § 371 of PCT International Application No. PCT/JP99/03092 which has an International filing date of Jun. 10, 1999, which designated the United States of America.

BACKGROUND OF THE INVENTION

1. Field of the Invention

The present invention relates to a method for continuously producing a dialkyl carbonate and a diol from a cyclic carbonate and an aliphatic monohydric alcohol. More particularly, the present invention is concerned with a method for continuously producing a dialkyl carbonate and a diol from a cyclic carbonate and an aliphatic monohydric alcohol, comprising continuously feeding a cyclic carbonate and an aliphatic monohydric alcohol to a continuous multi-stage distillation column, and continuously effecting a transesterification between the cyclic carbonate and the aliphatic monohydric alcohol in the presence of a transesterification catalyst in the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol in a liquid form from a lower portion of the multi-stage distillation column, wherein the transesterification is performed under conditions wherein: (a) the reaction pressure is $5 \times 10^4$ Pa or less, as measured at the inner bottom of the multi-stage distillation column; (b) the reaction temperature is in the range of from $-20°$ C. to less than $60°$ C., as measured at the inner bottom of the multi-stage distillation column; and (c) the multi-stage distillation column has an F-factor in the range of from 0.2 to 5.0. By the method of the present invention, continuous production of a dialkyl carbonate and a diol from a cyclic carbonate and an aliphatic monohydric alcohol can be easily performed with high productivity and high selectivity (i.e., a lowering of the occurrence of by-products), without using complicated equipment. Therefore, the method of the present invention is extremely advantageous from the commercial viewpoint.

2. Prior Art

With respect to the method for producing a dialkyl carbonate and a diol by reacting a cyclic carbonate with an aliphatic monohydric alcohol, various proposals have been made. Most of those proposals relate to the development of catalysts for the above reaction. Examples of such catalysts include alkali metals or basic compounds containing alkali metals [see U.S. Pat. No. 3,642,858, Unexamined Japanese Patent Application Laid-Open Specification No. 54-48715 (corresponding to U.S. Pat. No. 4,181,676)], tertiary aliphatic amines [see Unexamined Japanese Patent Application Laid-Open Specification No. 51-122025 (corresponding to U.S. Pat. No. 4,062,884)], thallium compounds [see Unexamined Japanese Patent Application Laid-Open Specification No. 54-48716 (corresponding to U.S. Pat. No. 4,307,032)], tin alkoxides (see Unexamined Japanese Patent Application Laid-Open Specification No. 54-63023), alkoxides of zinc, aluminum and titanium (see Unexamined Japanese Patent Application Laid-Open Specification No. 54-148726), a mixture of a Lewis acid with a nitrogen-containing organic base (see Unexamined Japanese Patent Application Laid-Open Specification No. 55-64550), phosphine compounds (see Unexamined Japanese Patent Application Laid-Open Specification No. 55-64551), quaternary phosphonium salts (see Unexamined Japanese Patent Application Laid-Open Specification No. 56-10144), cyclic amidines [see Unexamined Japanese Patent Application Laid-Open Specification No. 59-106436 (corresponding to U.S. Pat. No. 4,681,967, EP 110629B, and DE 3366133G)], compounds of zirconium, titanium and tin [see Unexamined Japanese Patent Application Laid-Open Specification No. 63-41432 (corresponding to U.S. Pat. No. 4,661,609, EP 255252B1 and DE 3781742G)], a solid, strongly basic anion-exchanger containing a quaternary ammonium group (see Unexamined Japanese Patent Application Laid-Open Specification No. 63-238043), a solid catalyst selected from the group consisting of a tertiary amine- or quaternary ammonium group-containing ion-exchange resin, a strongly acidic or a weakly acidic ion-exchange resin, a silica impregnated with a silicate of an alkali metal or an alkaline Dearth metal, and a zeolite exchanged with ammonium ion [see Unexamined Japanese Patent Application Laid-Open Specification No. 64-31737 (corresponding to U.S. Pat. No. 4,691,041)], a homogeneous catalyst selected from the group consisting of tertiary phosphine, tertiary arsine, tertiary stibine, a divalent sulfur compound and a selenium compound (see U.S. Pat. No. 4,734,518).

With respect to the method for conducting the above-mentioned reaction between a cyclic carbonate and a diol, the below-mentioned four types of methods (1) to (4) have conventionally been proposed. Hereinbelow, explanation is made with respect to such methods (1) to (4), taking as an example the production of dimethyl carbonate and ethylene glycol by the reaction between ethylene carbonate and methanol, which is a representative example of reactions between cyclic carbonates and diols.

(1) A completely batchwise method.
(2) A batchwise method using a reaction vessel provided at an upper portion thereof with a distillation column.
(3) A liquid flow method using a tubular reactor.
(4) A reactive distillation method.

The completely batchwise method (1) is a method in which ethylene carbonate, methanol and a catalyst are fed to an autoclave as a batchwise reaction vessel, and a reaction is performed at a reaction temperature higher than the boiling point of methanol under pressure for a predetermined period of time [see U.S. Pat. No. 3,642,858, Unexamined Japanese Patent Application Laid-Open Specification No. 54-48715 (corresponding to U.S. Pat. No. 4,181,676, EP 1082B and DE 2860078G), Unexamined Japanese Patent Application Laid-Open Specification No. 54-63023, Unexamined Japanese Patent Application Laid-Open Specification No. 54-148726, Unexamined Japanese Patent Application Laid-Open Specification No. 55-64550, Unexamined Japanese Patent Application Laid-Open Specification No. 55-64551 and Unexamined Japanese Patent Application Laid-Open Specification No. 56-10144].

The batchwise method (2), using an apparatus comprising a reaction vessel provided at an upper portion thereof with a distillation column, is a method in which ethylene carbonate, methanol and a catalyst are fed to the reaction vessel, and a reaction is performed by heating the contents of the reaction vessel to a predetermined temperature. In this method, the produced dimethyl carbonate and methanol form a minimum boiling point azeotropic mixture having a boiling point of $63°$ C./760 mmHg. The boiling point of methanol per se is $64.6°$ C./760 mmHg. In this method, the reaction is performed by using an excess amount of methanol in the reaction system, so that the resultant reaction products can be separated into the azeotropic mixture and methanol, due to the difference in boiling point therebetween, by means of the distillation column provided at the upper portion of the reaction vessel. Specifically, a gaseous mixture of dimethyl carbonate and methanol, which is formed in the reaction vessel, is allowed to ascend inside the distillation column, and during the ascending of the gaseous mixture, the gaseous mixture is caused to separate into a gaseous azeotropic mixture and liquid methanol. Then, the gaseous azeotropic mixture is distilled from the top of the distillation column while the liquid methanol flows down to the reaction vessel so as to be recycled to the reaction system in the reaction vessel.

The liquid flow method (3) is a method in which a solution of ethylene carbonate in methanol is continuously fed to a tubular reactor to perform a reaction at a predetermined reaction temperature in the tubular reactor, and the resultant liquid reaction mixture containing the unreacted materials (i.e., ethylene carbonate and methanol) and the reaction products (i.e., dimethyl carbonate and ethylene glycol) is continuously withdrawn through an outlet of the reactor. This method has conventionally been conducted in two different manners in accordance with the two types of catalyst used. That is, one manner consists in passing a mixture of a solution of ethylene carbonate in methanol and a solution of a homogenous catalyst in a solvent through a tubular reactor to perform a reaction, thereby obtaining a reaction mixture, and separating the catalyst from the obtained reaction mixture [see Unexamined Japanese Patent Application Laid-Open Specification No. 63-41432 (corresponding to U.S. Pat. No. 4,661,609, EP 255252B1 and DE 3781742G) and U.S. Pat. No. 4,734,518]. The other manner consists in performing the reaction in a tubular reactor having a heterogeneous catalyst securely placed therein [see Unexamined Japanese Patent Application Laid-Open Specification No. 63-238043 and Unexamined Japanese Patent Application Laid-Open Specification No. 64-31737 (corresponding to U.S. Pat. No. 4,691,041, EP 298167B1 and DE 3781796G)].

The reactive distillation method (4) is a method in which each of ethylene carbonate and methanol is continuously fed to a multi-stage distillation column to perform a reaction in a plurality of stages of the distillation column in the presence of a catalyst, while continuously effecting separation between the produced dimethyl carbonate and the produced ethylene glycol [see Unexamined Japanese Patent Application Laid-Open Specification No. 4-198141, Unexamined Japanese Patent Application Laid-Open Specification No. 4-230243, Unexamined Japanese Patent Application Laid-Open Specification No. 5-213830 (corresponding to DE 4129316A1, U.S. Pat. No. 5,231,212 and EP 530615A3) and Unexamined Japanese Patent Application Laid-Open Specification No. 6-9507 (corresponding to U.S. Pat. No. 5,359,118, EP 569812A1 and DE 4216121A1)].

However, the above-mentioned conventional methods (1) to (4) have their respective problems as described below.

In the case of each of the completely batchwise method (1) and the flow method (3) using a tubular reactor, it is impossible to achieve a higher conversion of ethylene carbonate than the conversion of ethylene carbonate at the equilibrium state of reaction (the latter conversion is dependent on the composition ratio of the feedstocks fed to the reactor and the reaction temperature). For example, in Example 1 of Unexamined Japanese Patent Application Laid-Open Specification No. 63-41432 (corresponding to U.S. Pat. No. 4,661,609, EP 255252B1 and DE 3781742G) which is directed to a continuous flow reaction method using a tubular reactor and wherein the flow reaction is conducted at 130° C. using a feedstock mixture having a methanol/ethylene carbonate molar ratio of 4/1, the conversion of ethylene carbonate is only 25%. This means that large amounts of unreacted ethylene carbonate and unreacted methanol, which are contained in the reaction mixture, need to be separated and recovered, which in turn are recycled to the reactor. Actually, in the method disclosed in Unexamined Japanese Patent Application Laid-Open Specification No. 64-31737 (corresponding to U.S. Pat. No. 4,691,041, EP 298167B1 and DE 3781796G), various apparatuses are used for the separation, purification, recovery and recycling of the unreacted compounds.

As described below in detail, the batchwise method (2) using a reaction vessel provided at an upper portion thereof with a distillation column has problems in that the reaction must be conducted for a prolonged period of time and, therefore, a large amount of methanol needs to be used for preventing the lowering of the selectivity for the desired products.

In method (2), in order to compensate for the methanol distilled as an azeotropic mixture of the methanol and the produced dimethyl carbonate, the continuous or batchwise addition of supplemental methanol to the reaction vessel is optionally conducted. However, irrespective of whether or not such an addition of supplemental methanol is conducted, the reaction per se is performed only in a batch-type reaction vessel. That is, in this method, the reaction is batchwise performed under reflux for a prolonged period of time as long as 3 to 20 hours.

In this method, the dimethyl carbonate, which is one of the reaction products, is continuously withdrawn out of the reaction system, whereas the ethylene glycol, which is another reaction product, remains together with the unreacted ethylene carbonate in the reaction system containing the catalyst for a long period of time. This long residence time of the ethylene glycol and the ethylene carbonate in the reaction system causes side reactions to thereby produce polyethylene glycols, such as diethylene glycol and triethylene glycol. For preventing the occurrence of such side reactions and the lowering of the selectivity for the desired products, it is necessary to use a large excess of methanol, relative to the amount of the ethylene carbonate which is batchwise fed to the reaction vessel. In fact, in the conventionally proposed methods, the following examples are noted in which a large excess of methanol is used; that is, use is made of methanol in excess amounts (in terms of the number of moles of methanol per mole of ethylene carbonate or propylene carbonate), such as 14 moles (U.S. Pat. No. 3,803,201), 17 moles (Unexamined Japanese Patent Application Laid-Open Specification No. 1-311054), 22 moles [Unexamined Japanese Patent Application Laid-Open Specification No. 51-122025 (corresponding to U.S. Pat. No. 4,062,884 and DE 2615665B)], and 23 moles [Unexamined Japanese Patent Application Laid-Open Specification No. 54-48716 (corresponding to U.S. Pat. No. 4,307,032, EP 1083B and DE 2860142G)].

In the case of the reactive distillation method (4), it is possible to perform a reaction with high conversion, as compared to methods (1), (2) and (3). In fact, it has been reported that, when the reactive distillation is conducted using a large amount of pure methanol (containing no dimethyl carbonate), relative to the amount of ethylene carbonate, i.e., an amount such that the methanol/ethylene carbonate molar ratio is 9 to 10, the conversion of the ethylene carbonate reaches 100% [see Example 1 of Unexamined Japanese Patent Application Laid-Open Specification No. 4-198141 and Example 11 of Unexamined Japanese Patent Application Laid-Open Specification No. 5-213830 (corresponding to U.S. Pat. No. 5,231,212, EP 530615A3 and DE 4129316A1)].

In method (4), the produced dimethyl carbonate is distilled from the distillation column as a low boiling point product together with the unreacted methanol. Dimethyl carbonate and methanol form an azeotropic mixture. Therefore, the separation of the produced dimethyl carbonate from the gaseous reaction mixture distilled from the distillation column is conducted by special separation methods, such as a distillation method conducted under pressure [Unexamined Japanese Patent Application Laid-Open Specification No. 51-108019 (corresponding to DE 2607003B)]. Generally, by this method, dimethyl carbonate containing no methanol can be obtained, whereas methanol can be obtained only in the form of a mixture thereof with dimethyl carbonate. Therefore, it is difficult to obtain pure methanol containing substantially no dimethyl carbonate. For example, in the Examples of the above-mentioned Unexamined Japanese Patent Application Laid-Open Specification No. 51-108019 (corresponding to DE 2607003B), a methanol/dimethyl carbonate mixture (weight ratio: 70/30) is separated by distillation, and pure dimethyl carbonate is obtained as a column bottom product. However, as a product distilled from the column top, only a methanol/dimethyl carbonate mixture (weight ratio: 95/5) is obtained.

As can be seen from the above, for obtaining pure methanol, an additional separation process needs to be conducted. Therefore, from the viewpoint of ease in practicing a commercial scale production of dimethyl carbonate, it has been strongly desired to develop a method in which the methanol/dimethyl carbonate mixture as such can be used as a feedstock instead of pure methanol.

However, heretofore, only a few techniques have been known, in which only a methanol/dimethyl carbonate mixture is used as a feedstock in method (4). For example, there can be mentioned the method described in Example 5 of Unexamined Japanese Patent Application Laid-Open Specification No. 5-213830 (corresponding to U.S. Pat. No. 5,231,212, EP 530615A3 and DE 4129316A1). However, in Example 5 of this Unexamined Japanese Patent Application Laid-Open Specification No. 5-213830, in which a methanol/dimethyl carbonate mixture (weight ratio: 70/30) is used, the conversion of ethylene carbonate is only 62.8% (calculated from the data of the composition of the product mixture obtained at the column bottom). The reason for such poor conversion resides in that, since the reaction between ethylene carbonate and methanol is an equilibrium reaction, the presence of dimethyl carbonate (which is a reaction product of the above reaction) in the reaction system causes a lowering in the conversion of the ethylene carbonate. Therefore, this method has a problem in that the larger the amount of dimethyl carbonate recycled to the reaction system, the longer the reaction time (residence time) required for achieving a desired conversion and the larger the amount of methanol required for achieving a desired conversion.

Accordingly, in the production of a dialkyl carbonate and a diol from a cyclic carbonate and an aliphatic monohydric alcohol by using method (4) and by making use of recycled methanol in the form of a methanol/dimethyl carbonate mixture, for achieving a complete conversion of ethylene carbonate, pure methanol needs to be supplied in addition to the methanol/dimethyl carbonate mixture as in Unexamined Japanese Patent Application Laid-Open Specification No. 6-9507 (corresponding to U.S. Pat. No. 5,359,118, EP 569812A1 and DE 4216121A1).

However, when the methanol/dimethyl carbonate mixture is used in combination with pure methanol, in addition to the main operation for obtaining the desired products, an additional complicated operation to separate the methanol/dimethyl carbonate azeotropic mixture into components thereof for obtaining pure methanol containing substantially no dimethyl carbonate needs to be conducted [for example, such an additional operation needs to be conducted using, in combination, two distillation columns which have different operation pressures (see Unexamined Japanese Patent Application Laid-Open Specification No. 2-212456)]. In fact, in the above-mentioned Unexamined Japanese Patent Application Laid-Open Specification No. 6-9507 (corresponding to U.S. Pat. No. 5,359,118, EP 569812A1 and DE 4216121A1), pure methanol is obtained by the above-mentioned additional complicated operation and used.

As mentioned above, in the case of method (4), it is possible to perform a reaction with high conversion, as compared to methods (1), (2) and (3). However, method (4) has a problem in that the productivity has not been satisfactorily high. Further, method (4) also has a problem in that the occurrence of by-products, such as dialkylene glycol and 2-alkoxyethanol, has not been able to be reduced (e.g., when ethylene carbonate and methanol are used as feedstocks, diethylene glycol and methoxyethanol are by-produced).

For solving the above-mentioned problems of method (4), a proposal has been made wherein a mixture of methanol and dimethyl carbonate is reacted with ethylene carbonate so as to cause the conversion of ethylene carbonate to become less than 100% and the unreacted ethylene carbonate is hydrolyzed to form ethylene glycol, thereby producing dimethyl carbonate and high purity ethylene glycol with high productivity while removing the need to recycle the unreacted ethylene carbonate [see WO 97/23445 (corresponding to U.S. Pat. No. 5,847,189 and EP 0889025A1)]. However, this method requires a hydrolysis reactor or the like, in addition to a distillation column. That is, this method requires complicated equipment.

As can be understood from the above, no method has heretofore been proposed for continuously producing a dialkyl carbonate and a diol, each with high productivity and high selectivity (i.e., a lowering of the occurrence of by-products), from a cyclic carbonate and an aliphatic monohydric alcohol by using only simple equipment.

SUMMARY OF THE INVENTION

The present inventors have made extensive and intensive studies with a view toward developing a method which is free from the above problems accompanying the prior art. Specifically, the studies have been made in connection with a continuous method which comprises continuously feeding a cyclic carbonate and an aliphatic monohydric alcohol to a continuous multi-stage distillation column, and continuously effecting a transesterification between the cyclic carbonate and the aliphatic monohydric alcohol in the presence of a transesterification catalyst in the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol in a liquid form from a lower portion of the multi-stage distillation column. As a result, it has unexpectedly been found that, when the transesterification is performed under conditions wherein:

(a) the reaction pressure is $5 \times 10^4$ Pa or less, as measured at the inner bottom of the multi-stage distillation column, (b) the reaction temperature is in the range of from $-20°$ C. to less than $60°$ C., as measured at the inner bottom of the multi-stage distillation column, and (c) the multi-stage distillation column has an F-factor in the range of from 0.2 to 5.0, the F-factor being represented by the following formula (1):

$$\text{F-factor} = u_g \, (\rho_g)^{1/2} \tag{1}$$

wherein $u_g$ represents the gas velocity (m/s) in the multi-stage distillation column and $\rho_g$ represents the gas density (kg/m$^3$) in the multi-stage distillation column, it becomes possible to achieve the above objective, i.e., to continuously produce a dialkyl carbonate and a diol, each with high productivity and high selectivity, without using complicated equipment, even when the aliphatic monohydric alcohol/cyclic carbonate molar ratio is low. The present invention has been made, based on this novel finding.

Accordingly, it is a primary object of the present invention to provide a novel method for continuously producing a dialkyl carbonate and a diol, each with high productivity and high selectivity (i.e., a lowering of the occurrence of by-products), from an aliphatic monohydric alcohol and a cyclic carbonate without using complicated equipment.

The foregoing and other objects, features and advantages of the present invention will be apparent from the following detailed description and appended claims taken in connection with the accompanying drawing.

Figure 1:
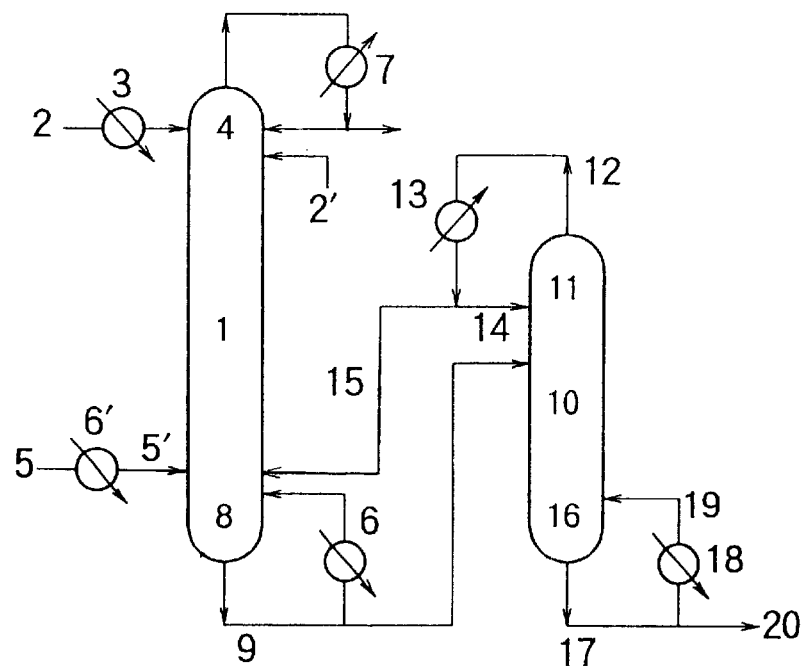
FIG. 1 is a diagram showing the system which was used for practicing Examples 1 to 7 and Comparative Examples 1 to 3 of the present application.

DESCRIPTION OF REFERENCE NUMERALS 1 continuous multi-stage distillation column
2, 2' conduit
3 preheater
4 top of column
5, 5' conduit
6 reboiler
6' evaporator
7 condenser
8 bottom of column
9 conduit
10 low boiling point mixture-recovering column
11 top of column
12 conduit
13 condenser
14 conduit
15 conduit
16 bottom of column
17 conduit
18 reboiler
19 conduit
20 conduit
21 conduit
22 conduit
23 diol-separating column
24 top of column
25 conduit
26 condenser
27 conduit
28 bottom of column
29 conduit
30 reboiler
31 conduit
32 conduit
33 condenser
34 conduit
35 conduit
36 conduit
37 continuous hydrolysis reactor
38 conduit
39 gas-liquid separator
40 conduit

DETAILED DESCRIPTION OF THE INVENTION

In the present invention, there is provided a method for continuously producing a dialkyl carbonate and a diol from a cyclic carbonate and an aliphatic monohydric alcohol, comprising continuously feeding a cyclic carbonate represented by the following formula (A):

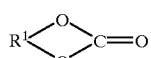
(A)

wherein $R^1$ is a divalent group represented by the formula $-(CH_2)_m-$, wherein m is an integer of from 2 to 6, which is unsubstituted or substituted with at least one substituent selected from the group consisting of a $C_1-C_{10}$ alkyl group and a $C_6-C_{10}$ aryl group, and an aliphatic monohydric alcohol represented by the following formula (B):

$$R^2OH \tag{B}$$

wherein $R^2$ is a monovalent aliphatic $C_1-C_{12}$ hydrocarbon group which is unsubstituted or substituted with at least one substituent selected from the group consisting of a $C_1-C_{10}$ alkyl group and a $C_6-C_{10}$ aryl group, to a continuous multi-stage distillation column, and continuously effecting a transesterification between the cyclic carbonate and the aliphatic monohydric alcohol in the presence of a transesterification catalyst in the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol in a liquid form from a lower portion of the multi-stage distillation column, wherein the transesterification is performed under conditions wherein:
(a) the reaction pressure is $5 \times 10^4$ Pa or less, as measured at the inner bottom of the multi-stage distillation column,
(b) the reaction temperature is in the range of from $-20°$ C. to less than $60°$ C., as measured at the inner bottom of the multi-stage distillation column, and
(c) the multi-stage distillation column has an F-factor in the range of from 0.2 to 5.0,
the F-factor being represented by the following formula (1):

$$\text{F-factor} = u_g (\rho_g)^{1/2} \tag{1}$$

wherein $u_g$ represents the gas velocity (m/s) in the multi-stage distillation column and $\rho_g$ represents the gas density (kg/m$^3$) in the multi-stage distillation column.

For an easy understanding of the present invention, the essential features and various preferred embodiments of the present invention are enumerated below.

1. A method for continuously producing a dialkyl carbonate and a diol from a cyclic carbonate and an aliphatic monohydric alcohol, comprising continuously feeding a cyclic carbonate represented by the following formula (A):

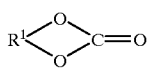

(A)

wherein $R^1$ is a divalent group represented by the formula $-(CH_2)_m-$, wherein m is an integer of from 2 to 6, which is unsubstituted or substituted with at least one substituent selected from the group consisting of a $C_1-C_{10}$ alkyl group and a $C_6-C_{10}$ aryl group,
and an aliphatic monohydric alcohol represented by the following formula (B):

$$R^2OH \tag{B}$$

wherein $R^2$ is a monovalent aliphatic $C_1-C_{12}$ hydrocarbon group which is unsubstituted or substituted with at least one substituent selected from the group consisting of a $C_1-C_{10}$ alkyl group and a $C_6-C_{10}$ aryl group,
to a continuous multi-stage distillation column, and continuously effecting a transesterification between the cyclic carbonate and the aliphatic monohydric alcohol in the presence of a transesterification catalyst in the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol in a liquid form from a lower portion of the multi-stage distillation column,
wherein the transesterification is performed under conditions wherein:
(a) the reaction pressure is $5 \times 10^4$ Pa or less, as measured at the inner bottom of the multi-stage distillation column,
(b) the reaction temperature is in the range of from $-20°$ C. to less than $60°$ C., as measured at the inner bottom of the multi-stage distillation column, and
(c) the multi-stage distillation column has an F-factor in the range of from 0.2 to 5.0,
the F-factor being represented by the following formula (1):

$$\text{F-factor} = u_g (\rho_g)^{1/2} \tag{1}$$

wherein $u_g$ represents the gas velocity (m/s) in the multi-stage distillation column and $\rho_g$ represents the gas density (kg/m$^3$) in the multi-stage distillation column.

2. The method according to item 1 above, wherein the F-factor is in the range of from 0.4 to 4.0.
3. The method according to item 2 above, wherein the F-factor is in the range of from 0.6 to 4.0.
4. The method according to any one of items 1 to 3 above, wherein the aliphatic monohydric alcohol contains a concomitant dialkyl carbonate in an amount of from 0 to 40% by weight, based on the total weight of the aliphatic monohydric alcohol and the concomitant dialkyl carbonate.
5. The method according to any one of items 1 to 4 above, wherein the cyclic carbonate is at least one carbonate selected from the group consisting of ethylene carbonate and propylene carbonate, and the aliphatic monohydric alcohol is methanol.
6. The method according to any one of items 1 to 5 above, wherein:
the cyclic carbonate is continuously fed, to an upper portion of the continuous multi-stage distillation column, in a liquid form or a gas-liquid mixture form, and
the aliphatic monohydric alcohol is continuously fed, to a lower portion of the continuous multi-stage distillation column, in a gaseous form or a gas-liquid mixture form, or in a gaseous form and in a liquid form individually.

In the method of the present invention, it becomes possible to advance the transesterification reaction with high productivity and high selectivity, as compared to those achieved by conventional methods, even when the aliphatic monohydric alcohol/cyclic carbonate molar ratio is low. Hereinbelow, the present invention will be explained in more detail.

The reaction performed in the present invention is a reversible, equilibrium transesterification reaction represented by the following reaction scheme (I), in which a dialkyl carbonate (C) and a diol (D) are produced from a cyclic carbonate (A) and an aliphatic monohydric alcohol (B):

(I)

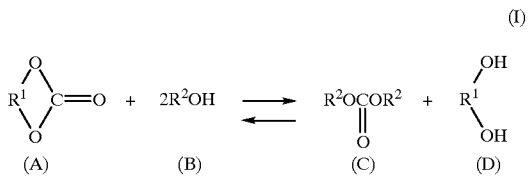

wherein:
$R^1$ is a divalent group represented by formula $-(CH_2)_m-$, in which m is an integer of from 2 to 6 and which is unsubstituted or substituted with at least one substituent selected from the group consisting of a $C_1-C_{10}$ alkyl group and a $C_6-C_{10}$ aryl group; and
$R^2$ represents a monovalent $C_1-C_{12}$ aliphatic group which is unsubstituted or substituted with at least one substituent selected from the group consisting of a $C_1$–$C_{10}$ alkyl group and a $C_6$–$C_{10}$ aryl group.

The above reaction is an exothermic reaction. The lower the reaction temperature, the larger the equilibrium constant becomes and, therefore, the higher the equilibrium concentrations of the products become. However, the lower the reaction temperature, the smaller the reaction rate becomes. Accordingly, for achieving and maintaining a satisfactory production rate while performing the reaction at a low temperature, it is necessary to increase the volume of the reaction system. An increase in the volume of the reaction system means a lowering of the productivity as defined in the present invention. In the present invention, the term "productivity" means a yield per unit volume of the reaction zone in a continuous multi-stage distillation column and per unit time, i.e., a space time yield in the reaction zone of a continuous multi-stage distillation column. When a plurality of continuous multi-stage distillation columns are used, the total volume of the continuous multi-stage distillation columns is used for calculation of the above-mentioned yield.

On the other hand, when it is desired to perform the reactive distillation under a low pressure without decreasing the feeding rate of the feedstocks, it is necessary to increase the diameter of the distillation column. For lowering the reaction pressure without decreasing the diameter of the distillation column, it is necessary to reduce the feeding rate of the feed-stocks. Thus, a decrease in the reaction pressure is expected to result in a lowering of the productivity.

Therefore, according to the conventional knowledge, an attempt to perform the reactive distillation under conditions wherein the reaction pressure is as low as $5 \times 10^4$ Pa or less and the reaction temperature is as low as less than 60° C., each as measured at the inner bottom of the multi-stage distillation column, is considered as being disadvantageous from the viewpoint of the productivity and the like. In fact, there has been no attempt in which the reactive distillation is conducted under the above pressure and temperature conditions, i.e., the conditions employed in the method of the present invention.

However, unexpectedly, it has for the first time been found that a dialkyl carbonate and a diol can be continuously produced with high productivity and high selectivity when the reactive distillation is performed under conditions wherein not only are the pressure and temperature of the column bottom maintained within the above-mentioned specific ranges, but also the distillation column has an F-factor in the range of from 0.2 to 5. Conventionally, the F-factor of a distillation column has been known as a parameter which relates to the stage efficiency of the distillation column [see OKagakukougaku jiten (Dictionary of Chemical Engineering), edited by Kagakukogaku Kyokai (Association of Chemical Engineering), p.55 (1986) (Maruzen Co., Ltd., Japan) and Chemical Engineer's Handbook, fifth edition, Section 18, p. 6 (1973) (McGraw-Hill Kogakusha, Ltd.)]. However, in the production of a dialkyl carbonate and a diol by the technique of reactive distillation using a distillation column, it has never been known at all that a correlation is present between the F-factor of the distillation column and the productivity of and the selectivity for the desired products. The present inventors have for the first time found that the F-factor of the distillation column employed in the reactive distillation has a correlation with the productivity of and the selectivity for the desired products.

Elucidation has not yet been made with respect to the reason why a high productivity and a high selectivity can be achieved by performing the present reaction by the reactive distillation under conditions wherein the reaction pressure and temperature fall within the above-mentioned respective specific ranges, as measured at the inner bottom of the multi-stage distillation column, and the F-factor of the distillation column is from 0.2 to 5.0. However, it is presumed that the efficiency of the reactive distillation is increased by employing such reaction conditions.

Examples of by-products formed in the reaction for producing a dialkyl carbonate and a diol from a cyclic carbonate and an aliphatic monohydric alcohol include a condensation product of ethylene glycol (EG), such as diethylene glycol (DEG) and triethylene glycol (TEG), and 2-methoxyethanol (2ME). When the content of DEG in ethylene glycol as the desired diol is high, a problem arises that a polyester which is produced using the ethylene glycol as a raw material has a non-uniformity in color. Further, when ethylene glycol (which is a bifunctional monomer) contains 2ME (which is monofunctional), a problem arises that 2ME acts as a terminator in a polyester-forming reaction using the ethylene glycol as a raw material and, hence, the obtained polyester is likely to have a low molecular weight. Therefore, it is disadvantageous that ethylene glycol contains such by-products as impurities. In general, the by-products contained in EG are separated therefrom by distillation. For example, since the boiling point of DEG (245° C.) is higher than that of EG (198° C.), when EG containing DEG is subjected to distillation, a purified EG containing a small amount of DEG is obtained as a column top fraction or a side cut (side stream) (i.e., a fraction withdrawn from a withdrawal port provided in a side wall of the distillation column), and DEG is obtained mainly as a column bottom liquid. In this distillation, for lowering the concentration of DEG in the purified EG, the distillation column is required to have a number of distillation stages. In addition, the concentration of DEG in the column bottom liquid is lowered by causing some amount of EG to go into the column bottom liquid; therefore, when the column bottom liquid is withdrawn from the column, EG is necessarily withdrawn from the column bottom together with by-produced DEG. This withdrawn column bottom liquid containing EG is generally wasted or incinerated, so that the yield of EG is lowered. Therefore, for preventing such a loss due to the occurrence of by-products, a high selectivity for the desired products is required.

With respect to the continuous multi-stage distillation column to be used in the method of the present invention, there is no particular limitation, as long as it is a distillation column which has two or more stages of distillation and which is capable of continuous distillation. In the present invention, the term "stages" is intended to include theoretical stages (theoretical plates). In the case of a distillation column having no substantive stages, such as a packed column, the value obtained by dividing the packing height by the height per theoretical stage (plate) (H.E.T.P.) (height equivalent to a theoretical plate) is considered as the number of stages. Examples of such continuous multi-stage distillation columns include plate type columns using a tray, such as a bubble-cap tray, a sieve tray, a valve tray, a counterflow tray, and packed type columns packed with various packings, such as a Raschig ring, a Lessing ring, a Pall ring, a Berl saddle, an Interlox saddle, a Dixon packing, a McMahon packing, a Heli pack, a Sulzer packing and Mellapak. Any column which is generally used as a continuous multi-stage distillation column can be utilized. Further, a mixed type of plate column and packed column, which comprises both a plate portion and a portion packed with packings, can also be preferably used. When a solid catalyst which is insoluble in the liquid phase in a distillation column is used, a packed column type distillation column, in which the solid catalyst is used in substitution for part or all of the packings, is preferably employed. As the continuous multi-stage distillation column to be used in the method of the present invention, the above-mentioned distillation columns can be used individually or in combination. When used in combination, a plurality of distillation columns may be connected in series or in parallel.

A cyclic carbonate to be used as a feedstock in the present invention is represented by formula (A) mentioned above. Examples of cyclic carbonates include alkylene carbonates, such as ethylene carbonate and propylene carbonate, 1,3-dioxacyclohexa-2-one, 1,3-dioxacyclohepta-2-one, and the like. Of these cyclic carbonates, ethylene carbonate and propylene carbonate are preferred because of their good availability. Ethylene carbonate is most preferred.

An aliphatic monohydric alcohol used as another feedstock in the present invention is a compound which is represented by formula (B) mentioned above and has a boiling point lower than that of the produced diol. The type of an aliphatic monohydric alcohol which can be used in the present invention varies depending on the type of the cyclic carbonate used. Examples of aliphatic monohydric alcohols include methanol, ethanol, propanol (isomers), allyl alcohol, butanol (isomers), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers) and the like. The above-mentioned aliphatic monohydric alcohol may be substituted with at least one substituent, such as a halogen atom, a lower alkoxy group, a cyano group, an alkoxycarbonyl group, an aryloxycarbonyl group, an acyloxy group or a nitro group.

Of these aliphatic monohydric alcohols, an alcohol having 1 to 6 carbon atoms is preferred. More preferred are monohydric alcohols having 1 to 4 carbon atoms, i.e., methanol, ethanol, propanol (isomers) and butanol (isomers). When ethylene carbonate or propylene carbonate is used as a cyclic carbonate, methanol and ethanol are preferred, and especially preferred is methanol.

In the present invention, the reaction represent ed by reaction scheme (I) is conducted by the technique of reactive distillation, that is, the reaction is conducted in a continuous multi-stage distillation column while separating a produced low boiling point mixture from the reaction system by distillati on.

In the method of the present invention, a catalyst is placed in the continuous multi-stage distillation column. The method for causing a catalyst to be present in the multi-stage distillation column is not particularly limited. For example, a homogeneous catalyst which is soluble in the reaction system under the reaction conditions can be caused to be present in the continuous multi-stage distillation column by continuously feeding the homogeneous catalyst to the continuous multi-stage distillation column. Alternatively, a heterogeneous catalyst (solid catalyst) which is insoluble in the reaction system under the reaction conditions, can be caused to be present in the continuous multi-stage distillation column by packing the solid catalyst in the continuous multi-stage distillation column. The above-mentioned homogeneous and heterogeneous catalysts can be used in combination.

When a homogeneous catalyst is continuously fed to the continuous multi-stage distillation column, it may be fed to the distillation column together with a feedstock cyclic carbonate and/or a feedstock aliphatic monohydric alcohol. Alternatively, the homogeneous catalyst may be fed to the distillation column at a position different from that at which the feedstock is fed. Further, the homogeneous catalyst can be fed to the distillation column at any position as long as the position is at least one theoretical stage (plate) above the column bottom. However, since the region where the reaction actually takes place in the continuous multi-stage distillation column is generally below the position at which the homogeneous catalyst is fed, it is preferred that the homogeneous catalyst is fed to the distillation column at the upper portion of the column.

When a heterogeneous solid catalyst is used as a catalyst, the catalyst can be packed in a desired amount at a desired position of the continuous multi-stage distillation column, as long as the catalyst layer present in the column has a height which corresponds to at least one theoretical stage (plate), preferably two or more theoretical stages (plates). A catalyst which can serve as a packing for the continuous multi-stage distillation column can also be used.

As a catalyst used in the present invention, various types of known catalysts can be used. Examples of such catalysts include alkali metals or alkaline earth metals, such as lithium, sodium, potassium, rubidium, cesium, magnesium, calcium, strontium and barium; basic compounds, such as hydrides, hydroxides, alkoxides, aryloxides and amides of alkali metals or alkaline earth metals; basic compounds, such as carbonates and hydrogencarbonates of alkali metals or alkaline earth metals and alkali metal or alkaline earth metal salts of organic acids; tertiary amines, such as triethylamine, tributylamine, trihexylamine and benzyldiethylamine; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine and alkyltriazine; cyclic amidines, such as diazabicycloundecene (DBU) and diazabicyclononene (DBN); thallium compounds, such as thallium oxide, thallium halides, thallium hydroxide, thallium carbonate, thallium nitrate, thallium sulfate and thallium salts of organic acids; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride and tin 2-ethylhexanoate; zinc compounds, such as dimethoxyzinc, diethoxyzinc, ethylenedioxyzinc and dibutoxyzinc; aluminum compounds, such as aluminum trimethoxide, aluminum triisopropoxide and aluminum tributoxide; titanium compounds, such as tetramethoxytitanium, tetraethoxytitanium, tetrabutoxytitanium, dichlorodimethoxytitanium, tetraisopropoxytitanium, titanium acetate and titanium acetylacetonate; phosphorus compounds, such as trimethylphosphine, triethylphosphine, tributylphosphine, triphenylphosphine, tributylmethylphosphonium halides, trioctylbutylphosphonium halides and triphenylmethylphosphonium halides; zirconium compounds, such as zirconium halides, zirconium acetylacetonate, zirconium alkoxides and zirconium acetate; lead and lead-containing compounds, e.g., lead oxides, such as PbO, $PbO_2$ and $Pb_3O_4$; lead sulfides, such as PbS, $Pb_2S_3$ and $PbS_2$; lead hydroxides, such as $Pb(OH)_2$, $Pb_3O_2(OH)_2$, $Pb_2[PbO_2(OH)_2]$ and $Pb_2O(OH)_2$; plumbites, such as Na$_2$PbO$_2$, K$_2$PbO$_2$, NaHPbO$_2$ and KHPbO$_2$; plumbates, such as Na$_2$PbO$_3$, Na$_2$H$_2$PbO$_4$, K$_2$PbO$_3$, K$_2$[Pb(OH)$_6$], K$_4$PbO$_4$, Ca$_2$PbO$_4$ and CaPbO$_3$; lead carbonates and basic salts thereof, such as PbCO$_3$ and 2PbCO$_3$.Pb(OH)$_2$; alkoxylead compounds and aryloxylead compounds, such as Pb(OCH$_3$)$_2$, (CH$_3$O)Pb(OPh) and Pb(OPh)$_2$; lead salts of organic acids, and carbonates and basic salts thereof, such as Pb(OCOCH$_3$)$_2$, Pb(OCOCH$_3$)$_4$ and Pb(OCOCH$_3$)$_2$.PbO.3H$_2$O; organolead compounds, such as Bu$_4$Pb, Ph$_4$Pb, Bu$_3$PbCl, Ph$_3$PbBr, Ph$_3$Pb (or Ph$_6$Pb$_2$), Bu$_3$PbOH and Ph$_2$PbO wherein Bu represents a butyl group and Ph represents a phenyl group; lead alloys, such as Pb—Na, Pb—Ca, Pb—Ba, Pb—Sn and Pb—Sb; lead minerals, such as galena and zinc blende; hydrates of these lead compounds; ion-exchangers, such as anion-exchange resins having tertiary amino groups, ion-exchange resins having amide groups, ion-exchange resins having at least one type of ion-exchange group selected from the group consisting of sulfonate, carboxylate and phosphate groups, and strongly basic solid anion-exchangers having quaternary ammonium groups as ion-exchange groups; solid inorganic compounds, such as silica, silica-alumina, silica-magnesia, aluminosilicate, gallium silicate, various types of zeolites, various types of metal-exchanged zeolites and ammonium-exchanged zeolites.

Among the above-mentioned solid catalysts, strongly basic anion-exchangers having quaternary ammonium groups as anion-exchange groups are preferred. Examples of such anion-exchangers include strongly basic anion-exchange resins having quaternary ammonium groups as anion-exchange groups, cellulose type strongly basic anion-exchangers having quaternary ammonium groups as anion-exchange groups and strongly basic anion-exchangers carried on an inorganic carrier which have quaternary ammonium groups as anion-exchange groups.

Of these strongly basic anion-exchange resins having quaternary ammonium groups as ion-exchange groups, styrene type strongly basic anion-exchange resins and the like are preferred. A styrene type strongly basic anion-exchange resin is comprised of a styrene/divinylbenzene copolymer as a base resin, and quaternary ammonium groups (type I or type II) as anion-exchange groups, examples of which are diagram-matically represented by the following formulae (II).

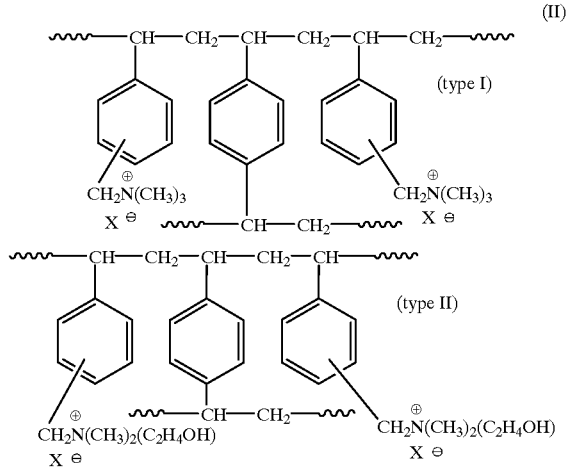

In above formulae (II), X represents an anion. Generally, X is at least one type of anion selected from the group consisting of F$^-$, Cl$^-$, Br$^-$, I$^-$, HCO$_3^-$, CO$_3^{2-}$, CH$_3$CO$_2^-$, HCO$_2^-$, IO$_3^-$, BrO$_3^-$ and ClO$_3^-$. It is preferred that X is selected from the group consisting of Cl$^-$, Br$^-$, HCO$_3^-$ and CO$_3^{2-}$. With respect to the structure of the base resin of the anion-exchange resin, either a gel type or a macroreticular type (MR type) can be used. However, because of the high resistance to organic solvents, the MR type is preferred.

Examples of cellulose type strongly basic anion-exchangers having quaternary ammonium groups as ion-exchange groups include cellulose type strongly basic anion-exchangers having ion-exchange groups of the structure represented by the formula: —OCH$_2$CH$_2$NR$_3$X, which exchangers are obtained by trialkylaminoethylation of a part or all of the hydroxyl groups of cellulose. In the above formula, R represents an alkyl group, for example, a methyl group, an ethyl group, a propyl group, a butyl group or the like, preferably a methyl group or an ethyl group; and X is as defined above.

The inorganic carrier-carried strongly basic anion-exchanger usable in the present invention, which has quaternary ammonium groups as ion-exchange groups, is an anion-exchanger having quaternary ammonium groups represented by the formula —O(CH$_2$)$_n$NR$_3$X wherein R and X are as defined above and n is usually an integer of from 1 to 6, preferably 2, which anion-exchanger can be prepared by the modification of a part or all of the hydroxyl groups on the surface of the inorganic carrier. Examples of inorganic carriers include silica, alumina, silica-alumina, titania and zeolite. Of these, silica, alumina and silica-alumina are preferred. Silica is most preferred. There is no limitation with respect to the method for the modification of hydroxyl groups on the surface of the inorganic carrier. For example, such a strongly basic anion-exchanger carried on an inorganic carrier can be obtained by subjecting an inorganic carrier and an aminoalcohol represented by the formula HO(CH$_2$)$_n$NR$_2$ to a dehydration reaction between them in the presence of a basic catalyst to thereby effect aminoalkoxylation, followed by the reaction of the resultant aminoalkoxylated inorganic carrier with an alkyl halide represented by the formula RX', wherein X' represents a halogen atom, preferably Cl, Br or I, to thereby convert the aminoalkoxy group into a —O(CH$_2$)$_n$NR$_3$X' group. The —O(CH$_2$)$_n$NR$_3$X' group is further converted to a —O(CH$_2$)$_n$NR$_3$X group having the desired anion X by an anion exchange reaction. When n is 2, an inorganic carrier is treated with N,N-dialkylaziridine so that the hydroxyl groups on the inorganic carrier are N,N-dialkylaminoethoxylated to obtain a —OCH$_2$CH$_2$NR$_2$ group, which is then converted to a —OCH$_2$CH$_2$NR$_3$X group by the above-mentioned method.

Commercially available solid, strongly basic anion-exchangers having quaternary ammonium groups as ion-exchange groups can be used in the present invention. When a commercially available solid, strongly basic anion-exchanger is used, it can be treated for anion-exchange with a desired anion species before it is used as a transesterification catalyst.

A solid catalyst comprised of a macroreticular or gel type organic polymer or an inorganic carrier, each having bonded thereto a heterocyclic group containing at least one nitrogen atom, is preferably used as a transesterification catalyst. Further, the above-mentioned solid catalyst can be treated for quaternarizing a part or all of the nitrogen-containing heterocyclic groups before it is used.

The amount of the catalyst to be used in the present invention varies depending on the type thereof. The homogeneous catalyst, which is soluble in the reaction system under the reaction conditions, is fed continuously in an amount of from 0.0001 to 50% by weight, based on the total weight of the feedstock cyclic carbonate and the feedstock aliphatic monohydric alcohol. When the solid catalyst is packed in the continuous multi-stage distillation column, it is packed preferably in an amount of from 0.01 to 75% by volume, based on the internal volume of the empty distillation column.

There is no particular restriction with respect to the method for continuously feeding a cyclic carbonate and an aliphatic monohydric alcohol to the continuous multi-stage distillation column, and any feeding method can be used as long as the feedstocks can be contacted with the catalyst in a region of the distillation column which corresponds to at least one stage, preferably at least two stages. That is, the cyclic carbonate and the aliphatic monohydric alcohol can be continuously fed to at least one stage of the continuous multi-stage distillation column through a desired number of feeding pipes onto a desired stage as long as the above requirement is satisfied. The cyclic carbonate and the monohydric alcohol may be fed either to the same stage of the distillation column or to separate stages individually. The feedstocks are continuously fed in a liquid form, a gaseous form or a gas-liquid mixture form. In addition to the feeding of the feedstocks to the continuous multi-stage distillation column as described above, additional feedstocks can be fed in a gaseous form to the lower portion of the distillation column intermittently or continuously. Also preferred is a method wherein the cyclic carbonate is continuously fed in a liquid form or a gas-liquid mixture form to a stage at a level higher than the stage where the catalyst is present, while the aliphatic monohydric alcohol is continuously fed to the lower portion of the distillation column in a gaseous form or a gas-liquid mixture form, or in a gaseous form and in a liquid form individually. In this case, some of the aliphatic monohydric alcohol may be contained in the cyclic carbonate. The amount of the aliphatic monohydric alcohol fed in a gaseous form to the lower portion of the distillation column is generally from 1 to 100% by weight, preferably from 5 to 100% by weight, more preferably from 20 to 100% by weight, based on the total weight of the aliphatic monohydric alcohol fed to the lower portion of the distillation column. As a method for feeding the aliphatic monohydric alcohol in a gaseous form to the lower portion of the distillation column, a method may be used wherein a reaction system solution is withdrawn from the lower portion of the distillation column and heated by a reboiler so as to be partially or completely evaporated, to thereby obtain a gas or gas-liquid mixture, and the obtained gas or gas-liquid mixture is returned to the lower portion of the distillation column. In this case, the position in the lower portion of the distillation column, from which a reaction system solution is withdrawn, may be or may not be the same as the position in the lower portion of the distillation column, to which the gas or gas-liquid mixture is returned.

In the present invention, a dialkyl carbonate and a diol as desired products may be contained in the feedstocks. For example, when the aliphatic monohydric alcohol contains a concomitant dialkyl carbonate, the amount of the concomitant dialkyl carbonate in the aliphatic monohydric alcohol is generally in the range of from 0 to 40% by weight, preferably from 0.1 to 30% by weight, more preferably from 1 to 20% by weight, based on the total weight of the aliphatic monohydric alcohol and the concomitant dialkyl carbonate.

The ratio of the aliphatic monohydric alcohol to the cyclic carbonate to be fed to the continuous multi-stage distillation column may vary depending on the type and quantity of the catalyst and the reaction conditions, but, in general, the molar ratio of the aliphatic monohydric alcohol to the cyclic carbonate may be in the range of from 0.01 to 1,000. For increasing the conversion of the cyclic carbonate, it is preferred to feed the aliphatic monohydric alcohol in an excess amount which is 2 times or more by mole the mole of the cyclic carbonate. However, too high a concentration of the aliphatic monohydric alcohol is undesirable because the size of the reaction equipment has to be large. Therefore, it is especially preferred to use the aliphatic monohydric alcohol in an amount which is 2 to 20 times by mole the mole of the cyclic carbonate.

The low boiling point mixture containing the dialkyl carbonate produced in the method of the present invention is continuously withdrawn from the upper portion of the continuous multi-stage distillation column in a gaseous form. The withdrawn gaseous mixture may be composed of a dialkyl carbonate alone or a mixture thereof with an aliphatic monohydric alcohol and a cyclic carbonate. Further, the withdrawn gaseous mixture may also contain a high boiling point product in a small amount.

A withdrawal port of the continuous multi-stage distillation column for withdrawing the gaseous low boiling point mixture containing the dialkyl carbonate is preferably provided at a position between the position from which the feedstocks are fed and the top of the distillation column, or in the top of the distillation column. It is more preferred to provide the withdrawal port for the low boiling point mixture in the top of the distillation column. A part of the low boiling point mixture withdrawn from the withdrawal port may be returned to the upper portion of the distillation column to thereby effect the so-called reflux operation. When the reflux ratio is increased by conducting this reflux operation, the distillation efficiency of a low boiling point product into a vapor phase is increased, thereby advantageously increasing the concentration of a low boiling point product in the withdrawn gaseous component. However, too much of an increase in the reflux ratio disadvantageously leads to an increase in the thermal energy required. Thus, the reflux ratio is generally chosen in the range of from 0 to 10, preferably from 0 to 5, more preferably from 0 to 3.

A diol produced in the method of the present invention is continuously withdrawn from a lower portion of the continuous multi-stage distillation column in a liquid form.

In the present invention, the upper portion of the continuous multi-stage distillation column means a portion between the top of the distillation column and a position at approximately half the height of the distillation column, and the upper portion includes the top of the column. The lower portion of the continuous multi-stage distillation column means a portion between the bottom of the distillation column and a position at approximately half the height of the distillation column, and the lower portion includes the bottom of the column.

The withdrawal port for withdrawing the reaction mixture containing the produced diol from the continuous multi-stage distillation column is positioned at a lower portion of the distillation column, preferably at the bottom of the distillation column. A part of the withdrawn reaction mixture may be recycled to the lower portion of the continuous multi-stage distillation column in a gaseous form or a gas-liquid mixture form by heating by means of a reboiler.

In the reaction conditions employed in the method of the present invention, the multi-stage distillation column has an F-factor in the range of from 0.2 to 5.0, the F-factor being represented by the following formula (1):

$$F\text{-factor} = u_g \, (\rho_g)^{1/2} \tag{1}$$

wherein $u_g$ represents the gas velocity (m/s) in the multi-stage distillation column and $\rho_g$ represents the gas density (kg/m$^3$) in the multi-stage distillation column. The F-factor of the distillation column is preferably in the range of from 0.4 to 4.0, more preferably from 0.6 to 4.0.

The rate at which a liquid flows down inside the continuous multi-stage distillation column and the above-mentioned gas velocity ($u_g$) in the multi-stage distillation column may be varied depending on the type of the distillation column, and on the type of the packing in the case of a packed column. However, the distillation column is generally operated so that no flooding or weeping occurs.

The gas density ($\rho_g$) in the multi-stage distillation column may be varied depending on the reaction temperature and pressure, and on the types of the cyclic carbonate and aliphatic monohydric alcohol used, but is generally in the range of from 0.01 to 2.0 kg/m$^3$, preferably from 0.1 to 0.8 kg/m$^3$.

In the method of the present invention, the reaction takes place within the continuous multi-stage distillation column. The amount of dialkyl carbonate produced depends on the amount of hold-up liquid in the distillation column. That is, when the height and diameter of a distillation column are not changed, a greater hold-up capacity is preferred because the greater the hold-up capacity, the longer the residence time of the liquid phase, namely, the time during which the reaction is effected. However, when the amount of the hold-up liquid is too large, the residence time becomes too long, so that side reactions and flooding are likely to occur. Accordingly, in the method of the present invention, the amount of the hold-up liquid of the continuous multi-stage distillation column varies depending on the distillation conditions and the type of the distillation column. Generally, however, the amount of the hold-up liquid is in the range of from 0.005 to 0.75 in terms of the volume ratio of the hold-up liquid to the empty continuous multi-stage distillation column.

In the method of the present invention, the average residence time of the liquid phase in the continuous multi-stage distillation column depends on the reaction conditions, and the type and inner structure (for example, the types of the plate and packing) of the continuous multi-stage distillation column, but is generally in the range of from 0.001 to 50 hours, preferably from 0.01 to 10 hours, more preferably from 0.05 to 5 hours.

In the method of the present invention, the reaction temperature is in the range of from −20° C. to less than 60° C., as measured at the inner bottom of the multi-stage distillation column. A preferred range of the reaction temperature varies depending on the types of the feedstocks and the reaction pressure, but is generally from 0° C. to less that 60° C.

In the method of the present invention, the reaction pressure, as measured at the inner bottom of the multi-stage distillation column, is generally 5×10$^4$ Pa or less, preferably from 1×10$^3$ Pa to 5×10$^4$ Pa, more preferably from 1×10$^4$ Pa to 5×10$^4$ Pa.

It is also possible to recycle a part of a reaction mixture withdrawn from the lower portion of the multi-stage distillation column to the multi-stage distillation column, so that a part of an unreacted cyclic carbonate and/or unreacted aliphatic monohydric alcohol can be recycled to the multi-stage distillation column. In this case, the reaction mixture withdrawn from the lower portion of the multi-stage distillation column, as such, may be fed to the multi-stage distillation column. Alternatively, a method may be used in which a part or all of the reaction mixture withdrawn from the lower portion of the multi-stage distillation column is subjected to separation using a distillation separation column thereby obtaining a column top fraction containing an unreacted cyclic carbonate and/or unreacted aliphatic monohydric alcohol and a column bottom liquid, and the column top fraction and/or the column bottom liquid is then fed to the multi-stage distillation column. For example, preferred is a method in which a reaction mixture withdrawn from the lower portion of the continuous multi-stage distillation column is introduced to a low boiling point mixture-recovering column which is comprised of a distillation column, to thereby obtain a mixture of an aliphatic monohydric alcohol and a dialkyl carbonate from the top of the recovering column, and then the mixture withdrawn from the top of the recovering column is continuously recycled to the multi-stage distillation column.

There is no particular limitation with respect to the position of an introduction port in the multi-stage distillation column, through which a reaction mixture withdrawn from the multi-stage distillation column is recycled to the multi-stage distillation column. However, when an unreacted aliphatic monohydric alcohol is recycled to the multi-stage distillation column, it is preferred that this introduction port is positioned at a lower portion of the multi-stage distillation column, and when an unreacted cyclic carbonate is recycled to the multi-stage distillation column, it is preferred that this introduction port is positioned at an upper portion of the multi-stage distillation column.

In the present invention, it is not necessary to use a solvent. However, for the purposes of, e.g., (1) facilitating the operation for performing the reaction and (2) efficiently obtaining a dialkyl carbonate and a diol by azeotropic distillation or extractive distillation, an appropriate inert solvent may be used as a reaction solvent, an azeotrope-forming agent or an extracting agent. Examples of inert solvents include an ether, an aliphatic hydrocarbon, an aromatic hydrocarbon, a halogenated aliphatic hydrocarbon and a halogenated aromatic hydrocarbon.

An inert gas, such as nitrogen, helium or argon, may be present in the reaction system. Further, for the purpose of promoting the distilling-off of a generated low boiling point reaction product, the above-mentioned inert gas or a gaseous form of an inert low boiling point organic compound may be introduced to the reaction system from a lower portion of the continuous multi-stage distillation column.

BEST MODE FOR CARRYING OUT THE INVENTION

The present invention will be described in greater detail with reference to the following Examples, Comparative Examples, Reference Example and Reference Comparative Example, which should not be construed as limiting the scope of the present invention.

In the following, the analysis of a reaction mixture was conducted by means of gas chromatograph GCA (manufactured and sold by Shimadzu Corporation, Japan) using column TC-1 (manufactured and sold by GL Science Inc., Japan). The yield of and selectivity for a product and the F-factor of a continuous multi-stage distillation column were measured in the following manner.

Yield and selectivity

The yield (%) of ethylene glycol is determined, based on the amount of the charged ethylene carbonate; the selectivity (%) for ethylene glycol is determined, based on the amount of the consumed ethylene carbonate; the yield (%) of dimethyl carbonate is determined, based on the amount of the charged ethylene carbonate; and the respective selectivities (%) for dimethyl carbonate, diethylene glycol and 2-methoxyethanol are determined, based on the amount of the consumed ethylene carbonate.

F-factor

The F-factor of a continuous multi-stage distillation column is represented by the following formula (1):

$$\text{F-factor} = u_g (\rho_g)^{1/2} \quad (1)$$

wherein $u_g$ represents the gas velocity (m/s) in the multi-stage distillation column and $\rho_g$ represents the gas density (kg/m³) in the multi-stage distillation column.

In the above formula (1), $u_g$ and $\rho_g$ can be determined by the following formulae (3) and (2), respectively:

$$\rho_g = P \cdot M / [R \cdot (273.16 + t)] \quad (2)$$

wherein P represents the reaction pressure (atm), as measured at the inner bottom of the multi-stage distillation column, M represents the average molecular weight (g/mol) of the feedstock fed in a gaseous form to a lower portion of the multi-stage distillation column, R represents the gas constant (liter·atm/K·mol), and t represents the reaction temperature (° C.), as measured at the inner bottom of the multi-stage distillation column;
and $$u_g = Q / (3{,}600 \, \text{Å} \cdot \rho_g) \quad (3)$$

wherein Q represents the mass velocity (kg/h) of the feedstock fed in a gaseous form to a lower portion of the multi-stage distillation column, and A represents the cross-sectional area (m²) of the multi-stage distillation column.

Thus, the F-factor of a distillation column can be calculated by formulae (1), (2) and (3) from the above-mentioned Q, A, P, M, R and t. (In the above calculations, when a reaction mixture is withdrawn from the multi-stage distillation column and heated by an evaporator or the like to obtain a gas or a gas-liquid mixture and the obtained gas or gas-liquid mixture is then returned to a lower portion of the multi-stage distillation column, the returned gas or the gas component of the returned gas-liquid mixture is excluded from the "feedstock fed in a gaseous form to a lower portion of the multi-stage distillation column" mentioned above.)

EXAMPLE 1

Using a production system as shown in FIG. 1, dimethyl carbonate (DMC) and ethylene glycol (EG) were continuously produced from ethylene carbonate (EC) and methanol (MeOH).

Dixon packings (3 mmφ) were packed in continuous multi-stage distillation column 1, which was comprised of a column equipped with a reboiler and a condenser, the column having an inner diameter of 4 cm (cross-sectional area: 0.00126 m²) and a packing height of 200 cm. EC was continuously fed in a liquid form to column top 4 of distillation column 1 through conduit 2 and preheater 3 at a flow rate of 776.2 g/h, and a 4.8% by weight solution of potassium hydroxide (as a catalyst) in ethylene glycol was also continuously fed in a liquid form through conduit 2' at a flow rate of 32.6 g/h, while continuously feeding a mixture of MeOH and DMC (MeOH/DMC weight ratio=97/3) in a gaseous form through conduit 5, evaporator 6' and conduit 5' at a flow rate of 2,267.7 g/h, to thereby effect a transesterification reaction. Continuous multi-stage distillation column 1 was operated under conditions wherein the reaction pressure and reaction temperature, each as measured at column bottom 8 thereof, were 45,600 Pa (0.45 atm) and 56° C., respectively. Average molecular weight M of the feedstock fed in a gaseous form to a lower portion of distillation column 1 (that is, the mixture of MeOH and DMC, fed in a gaseous form through conduit 5') was calculated by using the MeOH/DMC molar ratio (0.989/0.011) as follows.

$$M = 0.989 \times 32.04 + 0.011 \times 90.08 = 32.7$$

Therefore, gas density $\rho_g$ (kg/m³) and gas velocity $u_g$ (m/s) in distillation column 1 were calculated as follows:

$$\rho_g = 0.45 \times 32.7 / [0.08205 \times (273.16 + 56)] = 0.545$$

$$u_g = 2.2677 / (3{,}600 \times 0.00126 \times 0.545) = 0.917$$

wherein the value of mass velocity Q (2.2677) used in obtaining gas velocity $u_g$ is the mass velocity (2.2677 kg/h) of the gaseous mixture of MeOH and DMC fed through conduit 5'.

From the thus obtained gas density $\rho_g$ and gas velocity $u_g$, F-factor of distillation column 1 was calculated as follows.

$$\text{F-factor} = 0.917 \times (0.545)^{0.5} = 0.68$$

A gaseous mixture distilled from column top 4 of distillation column 1 was condensed by condenser 7. A part of the resultant condensate was refluxed to column top 4 of distillation column 1 (reflux ratio: 0.1), while recovering the remainder of the condensate (containing MeOH and DMC in concentrations of 66.8% by weight and 33.2% by weight, respectively) in a liquid form from the production system. The flow rate of the above condensate recovered from the system was maintained at 2,524 g/h by heating the column bottom liquid by means of reboiler 6. A liquid reaction mixture (containing MeOH, DMC, EG and EC in concentrations of 48.7% by weight, 9.2% by weight, 48.2% by weight and 2.0% by weight, respectively) was withdrawn from column bottom 8 of distillation column 1 at a flow rate of 1,165 g/h and fed to low boiling point mixture-recovering column 10 at a position 100 cm below the top of column 10 through conduit 9, wherein column 10 was comprised of a column having an inner diameter of 5 cm and a packing height of 200 cm and having packed therein Dixon packings (3 mmφ).

Low boiling point mixture-recovering column 10 was operated under conditions wherein the pressure of column top 11 thereof was 1.3×10³ Pa (10 torr) and the temperature of column bottom 16 thereof was 101° C. A gaseous mixture withdrawn from column top 11 of column 10 was condensed by condenser 13. A part of the resultant condensate was refluxed to column top 11 of column 10 through conduit 14 while returning, through conduit 15, the remainder of the condensate in a liquid form to column bottom 8 of continuous multi-stage distillation column 1 at a flow rate of 578.5 g/h. On the other hand, a part of a liquid withdrawn from column bottom 16 of column 10 was recovered from the production system through conduit 20 at a flow rate of 586.6 g/h, while the remainder of the withdrawn liquid was heated by reboiler 18 and returned to column 10 through conduit 19. The withdrawn liquid (bottom liquid of column 10) contained EG (including catalyst-derived EG), EC and by-produced diethylene glycol (DEG) in concentrations of 95.8% by weight, 4.0% by weight and 0.02% by weight, respectively. In the withdrawn liquid, 2-methoxyethanol (2ME) (as a possible by-product) was not detected.

From the above data, it can be seen that the conversion of EC was 97%, the yield of DMC was 97% (DMC was produced at a production rate of 770 g/h), the selectivity for DMC was not lower than 99.9%, the yield of EG was 97% (EG was produced at a production rate of 530.7 g/h), and the selectivity for EG was not lower than 99.9%. Also, the volume (V) of the reaction zone in continuous multi-stage distillation column 1 was calculated as follows: V=π×22× 200/1,000=2.513 liter. Therefore, the productivity of DMC in terms of the space time yield was: 770/2.51=307 g/liter·h. The conditions and results of the trans-esterification reaction are shown in Table 1.

EXAMPLE 2

Dimethyl carbonate (DMC) and ethylene glycol (EG) were continuously produced from ethylene carbonate (EC) and methanol (MeOH) by using substantially the same production system as in Example 1, except that continuous multi-stage distillation column 1 had an inner diameter of 5 cm (cross-sectional area: 0.00196 m$^2$) and a packing height of 135 cm. The operation for the production of DMC and EG was performed in substantially the same manner as in Example 1, except that the reaction conditions were as follows: EC was fed at a flow rate of 727.0 g/h; a 4.8% by weight solution of potassium hydroxide (as a catalyst) in ethylene glycol was fed at a flow rate of 30.2 g/h; a mixture of MeOH and DMC was fed through conduit 5 at a flow rate of 2,157.9 g/h; the reaction temperature of column bottom 8 was 55.7° C.; and gas density $\rho_g$ and gas velocity $u_g$ in distillation column 1 were 0.545 kg/m$^3$ and 0.560 m/s, respectively, and hence the F-factor of distillation column 1 was 0.41.

A liquid mixture obtained by condensation of a gaseous mixture withdrawn from column top 4 of distillation column 1 (hereinafter referred to simply as "column top condensate from column 1") (containing MeOH and DMC in concentrations of 67.2% by weight and 32.8% by weight, respectively) was obtained at a flow rate of 2,363 g/h.

A liquid reaction mixture (containing MeOH, DMC, EG and EC in concentrations of 47.4% by weight, 1.2% by weight, 48.7% by weight and 2.6% by weight, respectively) was withdrawn from column bottom 8 of distillation column 1 at a flow rate of 1,064.6 g/h and, as in Example 1, fed to low boiling point mixture-recovering column 10 which was operated under the same conditions as in Example 1. A part of a liquid mixture obtained by condensation of a gaseous mixture withdrawn from column top 11 of column 10 (hereinafter referred to simply as "column top condensate from column 10") was returned in a liquid form to column bottom 8 of distillation column 1 at a flow rate of 517.3 g/h. A part of a liquid withdrawn from column bottom 16 of column 10 was recovered from the production system through conduit 20 at a flow rate of 547.3 g/h. The withdrawn liquid (bottom liquid of column 10) contained EG, EC and by-produced diethylene glycol (DEG) in concentrations of 94.7% by weight, 5.0% by weight and 0.03% by weight, respectively. In the withdrawn liquid, 2-methoxyethanol (2ME) (as a possible by-product) was not detected.

From the above data, it can be seen that the conversion of EC was 96%, the yield of DMC was 96% (DMC was produced at a production rate of 710 g/h), the selectivity for DMC was not lower than 99.9%, the yield of EG was 96% (EG was produced at a production rate of 489 g/h), and the selectivity for EG was not lower than 99.9%. Also, the volume (V) of the reaction zone in continuous multi-stage distillation column 1 was calculated as follows: V=π×2.5$^2$× 135/1,000=2.65 liter. Therefore, the productivity of DMC in terms of the space time yield was: 710/2.65=268 g/liter·h. The conditions and results of the transesterification reaction are shown in Table 1.

COMPARATIVE EXAMPLE 1

Dimethyl carbonate (DMC) and ethylene glycol (EG) were continuously produced from ethylene carbonate (EC) and methanol (MeOH) in substantially the same manner as in Example 2, except that the reaction pressure of column bottom 8 of distillation column 1 was 101,000 Pa (1 atm) and that, as a result, the reaction temperature of column bottom 8 of distillation column 1 was 79.6° C., and gas density $\rho_g$ and gas velocity $u_g$ in distillation column 1 were 1.130 kg/m$^3$ and 0.270 m/s, respectively, and hence the F-factor of distillation column 1 was 0.29.

A column top condensate from column 1 (containing MeOH and DMC in concentrations of 74.1% by weight and 25.9% by weight, respectively) was obtained at a flow rate of 2,313 g/h.

A liquid reaction mixture [containing MeOH, DMC, EG, EC, diethylene glycol (DEG) and 2-methoxyethanol (2ME) in concentrations of 38.1% by weight, 1.0% by weight, 40.3% by weight, 20.3% by weight, 0.19% by weight and 0.009% by weight, respectively] was with-drawn from column bottom 8 of distillation column 1 at a flow rate of 987.4 g/h. A part of a column top condensate from column 10 (low boiling point mixture-recovering column) was returned in a liquid form to column bottom 8 of distillation column 1 at a flow rate of 385.7 g/h. A part of a liquid withdrawn from column bottom 16 of column 10 was recovered from the production system through conduit 20 at a flow rate of 601.7 g/h. The withdrawn liquid (bottom liquid of column 10) contained EG, EC, by-produced diethylene glycol (DEG) and by-produced 2-methoxyethanol (2ME) in concentrations of 66.1% by weight, 33.4% by weight, 0.31% by weight and 0.015% by weight, respectively.

From the above data, it can be seen that the conversion of EC was 72.4%, the yield of DMC was 72.0% (DMC was produced at a production rate of 535 g/h), the selectivity for DMC was 99.4%, the yield of EG was 72.0% (EG was produced at a production rate of 368.7 g/h), and the selectivity for EG was 99.4%. It can also be seen that the selectivities for by-produced diethylene glycol and by-produced 2-methoxyethanol were 0.60% and 0.020%, respectively. Further, the productivity of DMC in terms of the space time yield was: 535/2.65=202 g/liter·h. The conditions and results of the transesterification reaction are shown in Table 1.

As mentioned above, in Comparative Example 1, the reaction was performed under conditions wherein the reaction pressure and temperature of column bottom 8 of column 1 were 1.013×10$^5$ Pa (i.e., atmospheric pressure) and 79.6° C., respectively (which are higher than those in Example 2), and the F-factor of column 1 was 0.29 (which is lower than that in Example 2). A comparison between the results of such Comparative Example 1 and the results of Example 2 shows that the productivity of DMC in Comparative Example 1 (202 g·liter$^{-1}$·h$^{-1}$) is lower than that in Example 2 (268 g·liter$^{-1}$·h$^{-1}$) [i.e., 202/268=0.75 (times)], and the occurrence of the by-products in Comparative Example 1 is larger than that in Example 2, despite the fact that Comparative Example 1 employs the same production system as in Example 2.

COMPARATIVE EXAMPLE 2

Dimethyl carbonate (DMC) and ethylene glycol (EG) were continuously produced from ethylene carbonate (EC)

and methanol (MeOH) in substantially the same manner as in Example 2, except that a mixture of MeOH and DMC was fed to column bottom 8 of distillation column 1 through conduit 5 at a flow rate of 3,123 g/h and the reaction pressure of column bottom 8 of distillation column 1 was 101,000 Pa (1 atm) and that, as a result, the reaction temperature of column bottom 8 of distillation column 1 was 76.7° C., and gas density $\rho_g$ and gas velocity $u_g$ in distillation column 1 were 1.14 kg/m$^3$ and 0.388 m/s, respectively, and hence the F-factor of distillation column 1 was 0.41.

A column top condensate from column 1 (containing MeOH and DMC in concentrations of 78.4% by weight and 21.6% by weight, respectively) was obtained at a flow rate of 3,302 g/h.

A liquid reaction mixture [containing MeOH, DMC, EG, EC, diethylene glycol (DEG) and 2-methoxyethanol (2ME) in concentrations of 42.8% by weight, 1.1% by weight, 44.4% by weight, 11.4% by weight, 0.21% by weight and 0.0097% by weight, respectively] was with-drawn from column bottom 8 of distillation column 1 at a flow rate of 1,028 g/h. A part of a column top condensate from column 10 (low boiling point mixture-recovering column) was returned in a liquid form to column bottom 8 of distillation column 1 at a flow rate of 451.2 g/h. A part of a liquid withdrawn from column bottom 16 of column 10 was recovered from the production system through conduit 20 at a flow rate of 577.1 g/h. The withdrawn liquid (bottom liquid of column 10) contained EG, EC, by-produced diethylene glycol and by-produced 2-methoxyethanol in concentrations of 79.0% by weight, 20.31% by weight, 0.38% by weight and 0.017% by weight, respectively.

From the above data, it can be seen that the conversion of EC was 83.9%, the yield of DMC was 83.4% (DMC was produced at a production rate of 620 g/h), the selectivity for DMC was 99.4%, the yield of EG was 83.4% (EG was produced at a production rate of 427.3 g/h), and the selectivity for EG was 99.4%. It can also be seen that the selectivities for by-produced diethylene glycol and by-produced 2-methoxyethanol were 0.60% and 0.019%, respectively. Further, the productivity of DMC in terms of the space time yield was: 620/2.65=234 g/liter-h. The conditions and results of the transesterification reaction are shown in Table 1.

As mentioned above, in Comparative Example 2, the reaction was performed under conditions wherein the reaction pressure and temperature of column bottom 8 of column 1 were atmospheric pressure and 76.7° C., respectively (which are higher than those in Example 2), and the F-factor of column 1 was 0.41 (which is the same as in Example 2), wherein the F-factor was achieved by increasing the flow rate of a mixture of MeOH and DMC fed to column 1 through conduit 5 to a level higher than that in Example 2. A comparison between the results of such Comparative Example 2 and the results of Example 2 shows that the productivity of DMC in Comparative Example 2 (234 g·liter$^{-1}$·h$^{-1}$) is lower than that in Example 2 (268 g·liter$^{-1}$·h$^{-1}$)[i.e., 234/268=0.87 (times)], and the occurrence of the by-products in Comparative Example 2 is larger than that in Example 2, despite the fact that the amount of MeOH fed to distillation column 1 in Comparative Example 2 is larger than that in Example 2.

EXAMPLE 3

Dimethyl carbonate (DMC) and ethylene glycol (EG) were continuously produced from ethylene carbonate (EC) and methanol (MeOH) by using substantially the same production system as in Example 1, except that continuous multi-stage distillation column 1 had an inner diameter of 5.36 cm (cross-sectional area: 0.00225 m$^2$) and a packing height of 100 cm. The operation for the production of DMC and EG was performed in substantially the same manner as in Example 1, except that the reaction conditions we re as follows: EC was fed at a flow rate of 612.2 g/h; a 4.8% by weight solution of sodium hydroxide (as a catalyst)(instead of potassium hydroxide) in ethylene glycol was fed at a flow rate of 25.4 g/h (instead of 32.6 g/h); a mixture of MeOH and DMC was fed through conduit 5 at a flow rate of 1,737 g/h; the reaction temperature of column bottom 8 was 56.2° C.; and gas density $\rho_g$ and gas velocity $u_g$ in distillation column 1 were 0.545 kg/of and 0.393 m/s, respectively, and hence the F-factor of distillationo column 1 was 0.29.

A column top condensate from column 1 (containing MeOH and DMC in concentrations of 67.2% by weight and 32.8% by weight, respectively) was obtained at a flow rate of 1,902 g/h.

A liquid reaction mixture (containing MEOH, DMC, EG and EC in concentrations of 45.7% by weight, 1.2% by weight, 47.1% by weight and 6.0% by weight, respectively) was withdrawn from column bottom 8 of distillation column 1 at a flow rate of 888.7 g/h and, as in Example 1, fed to low boiling point mixture-recovering column 10 which was operated under the same conditions as in Example 1. A part of a column top condensate from column 10 (low boiling point mixture-recovering column) was returned in a liquid form to column bottom 8 of distillation column 1 at a flow rate of 416 g/h. A part of a liquid withdrawn from column bottom 16 of column 10 was recovered from the production system through conduit 20 at a flow rate of 472.7 g/h. The withdrawn liquid (bottom liquid of column 10) contained EG, EC and by-produced diethylene glycol (DEG) in concentrations of 88.5% by weight, 11.3% by weight and 0.02% by weight, respectively. In the withdrawn liquid, 2-methoxyethanol (2ME) (as a possible by-product) was not detected.

From the above data, it can be seen that the conversion of EC was 91.3%, the yield of DMC was 91.3% (DMC was produced at a production rate of 572 g/h), the selectivity for DMC was not lower than 99.9%, the yield of EG was 91.3% (EG was produced at a production rate of 394 g/h), and the selectivity for EG was not lower than 99.9%. Also, the volume (V) of the reaction zone in continuous multi-stage distillation column 1 was calculated as follows: V=π× 2.68$^2$×100/1,000=2.26 liter. Therefore, the productivity of DMC in terms of the space time yield was: 572/2.26=253 g/liter·h. The conditions and results of the transesterification reaction are shown in Table 1.

COMPARATIVE EXAMPLE 3

Dimethyl carbonate (DMC) and ethylene glycol (EG) were continuously produced from ethylene carbonate (EC) and methanol (MeOH) in substantially the same manner as in Example 3, except that a mixture of MeOH and DMC was fed to column bottom 8 of distillation column 1 through conduit 5 at a flow rate of 719 g/h and that, as a result, the reaction temperature of column bottom 8 of distillation column 1 was 55.9° C., and gas density $\rho_g$ and gas velocity $u_g$ in distillation column 1 were 0.545 kg/m$^3$ and 0.163 m/s, respectively, and hence the F-factor of distillation column 1 was 0.12.

A column top condensate from column 1 (containing MeOH and DMC in concentrations of 66.3% by weight and 33.7% by weight, respectively) was obtained at a flow rate of 789.3 g/h.

A liquid reaction mixture [containing MeOH, DMC, EG, EC and diethylene glycol (DEG) in concentrations of 42.3% by weight, 0.96% by weight, 19.3% by weight, 37.4% by weight and 0.02% by weight, respectively] was withdrawn from column bottom 8 of distillation column 1 at a flow rate of 998.9 g/h.

A part of a column top condensate from column 10 (low boiling point mixture-recovering column) was returned in a liquid form to column bottom 8 of distillation column 1 at a flow rate of 431.8 g/h. A part of a liquid withdrawn from column bottom 16 of column 10 was recovered from the production system through conduit 20 at a flow rate of 567.1 g/h. The withdrawn liquid (bottom liquid of column 10) contained EG, EC and by-produced diethylene glycol (DEG) in concentrations of 33.9% by weight, 65.86% by weight and 0.02% by weight, respectively.

From the above data, it can be seen that the conversion of EC was 39%, the yield of DMC was 38.9% (DMC was produced at a production rate of 244 g/h) and the yield of EG was 38.9% (EG was produced at a production rate of 168.2 g/h). Further, the productivity of DMC in terms of the space time yield was: 244/2.26=108 g/liter·h. The conditions and results of the transesterification reaction are shown in Table 1.

As described above, in Comparative Example 3, the flow rate of a mixture of MeOH and DMC fed to distillation column 1 through conduit 5 is decreased so as to achieve an F-factor (0.12) which is lower than that in Example 3. A comparison between the results of such Comparative Example 3 and the results of Example 3 shows that the productivity of DMC in Comparative Example 3 (108 g·liter$^{-1}$·h$^{-1}$) is lower than that in Example 3 (253 g·liter$^{-1}$·h$^{-1}$) [i.e., 108/253=0.43 (times)].

EXAMPLE 4

Using the same production system as in Example 1, dimethyl carbonate (DMC) and ethylene glycol (EG) were continuously produced from ethylene carbonate (EC) and methanol (MeOH) in substantially the same manner as in Example 1, except that the reaction conditions were as follows: EC was fed at a flow rate of 988.6 g/h; a 4.8% by weight solution of potassium hydroxide (as a catalyst) in ethylene glycol was fed at a flow rate of 61.5 g/h; a mixture of MeOH and DMC was fed through conduit 5 at a flow rate of 2,580.9 g/h; the reaction pressure and temperature of column bottom 8 were 30,400 Pa (0.3 atm) and 47.1° C., respectively; and gas density $\rho_g$ and gas velocity $u_g$ in distillation column 1 were 0.373 kg/m$^3$ and 1.524 m/s, respectively, and hence the F-factor of distillation column 1 was 0.94.

A column top condensate from column 1 (containing MeOH and DMC in concentrations of 65.1% by weight and 34.9% by weight, respectively) was obtained at a flow rate of 2,891 g/h.

A liquid reaction mixture (containing MeOH, DMC, EG and EC in concentrations of 44.8% by weight, 1.1% by weight, 48.5% by weight and 5.4% by weight, respectively) was withdrawn from column bottom 8 of distillation column 1 at a flow rate of 1,446 g/h and, as in Example 1, fed to low boiling point mixture-recovering column 10 which was operated under the same conditions as in Example 1. A part of a column top condensate from column 10 (low boiling point mixture-recovering column) was returned in a liquid form to column bottom 8 of distillation column 1 at a flow rate of 664.2 g/h. A part of a liquid withdrawn from column bottom 16 of column 10 was recovered from the production system through conduit 20 at a flow rate of 781.8 g/h. The withdrawn liquid (bottom liquid of column 10) contained EG, EC and by-produced diethylene glycol (DEG) in concentrations of 89.6% by weight, 10.0% by weight and 0.01% by weight, respectively. In the withdrawn liquid, 2-methoxyethanol (2ME) (as a possible by-product) was not detected.

From the above data, it can be seen that the conversion of EC was 92%, the yield of DMC was 92% (DMC was produced at a production rate of 932 g/h), the selectivity for DMC was not lower than 99.9%, the yield of EG was 92% (EG was produced at a production rate of 642 g/h), and the selectivity for EG was not lower than 99.9%. Further, the productivity of DMC in terms of the space time yield was: 932/2.51=371 g/liter·h. The conditions and results of the trans-esterification reaction are shown in Table 1.

EXAMPLE 5

Dimethyl carbonate (DMC) and ethylene glycol (EG) were continuously produced from ethylene carbonate (EC) and methanol (MeOH) by using substantially the same production system as in Example 1, except that continuous multi-stage distillation column 1 had an inner diameter of 5 cm (cross-sectional area: 0.00196 m$^2$) and a packing height of 135 cm. The operation for the production of DMC and EG was performed in substantially the same manner as in Example 1, except that the reaction conditions were as follows: EC was fed at a flow rate of 938.9 g/h; a 4.8% by weight solution of potassium hydroxide (as a catalyst) in ethylene glycol was fed at a flow rate of 58.7 g/h; a mixture of MeOH and DMC was fed through conduit 5 at a flow rate of 2,581 g/h; the reaction pressure and temperature of column bottom 8 were 30,400 Pa (0.3 atm) and 47° C., respectively; and gas density $\rho_g$ and gas velocity $u_g$ in distillation column 1 were 0.373 kg/m$^3$ and 0.978 m/s, respectively, and hence the F-factor of distillation column 1 was 0.60.

A column top condensate from column 1 (containing MeOH and DMC in concentrations of 66.6% by weight and 33.4% by weight, respectively) was obtained at a flow rate of 2,832 g/h.

A liquid reaction mixture (containing MeOH, DMC, EG and EC in concentrations of 45.0% by weight, 1.1% by weight, 47.3% by weight and 6.4% by weight, respectively) was withdrawn from column bottom 8 of distillation column 1 at a flow rate of 1,385.2 g/h and, as in Example 1, fed to low boiling point mixture-recovering column 10 which was operated under the same conditions as in Example 1. A part of a column top condensate from column 10 was returned in a liquid form to column bottom 8 of distillation column 1 at a flow rate of 638.5 g/h. A part of a liquid withdrawn from column bottom 16 of column 10 was recovered from the production system through conduit 20 at a flow rate of 746.7 g/h. The withdrawn liquid (bottom liquid of column 10) contained EG, EC and by-produced diethylene glycol (DEG) in concentrations of 87.7% by weight, 12.0% by weight and 0.01% by weight, respectively. In the withdrawn liquid, 2-methoxyethanol (2ME) (as a possible by-product) was not detected.

From the above data, it can be seen that the conversion of EC was 90.5%, the yield of DMC was 90.5% (DMC was produced at a production rate of 869 g/h), the selectivity for DMC was not lower than 99.9%, the yield of EG was 90.5% (EG was produced at a production rate of 599 g/h), and the selectivity for EG was not lower than 99.9%. Also, the volume (V) of the reaction zone in continuous multi-stage distillation column was calculated as follows: V=π×2.5$^2$× 135/1,000=2.65 liter. Therefore, the productivity of DMC in terms of the space time yield was: 869/2.65=328 g/liter·h. The conditions and results of the trans-esterification reaction are shown in Table 1.

EXAMPLE 6

Dimethyl carbonate (DMC) and ethylene glycol (EG) were continuously produced from ethylene carbonate (EC)

and methanol (MeOH) by using substantially the same production system as in Example 3, except that a feed port for a mixture of MeOH and DMC which was fed through conduit 5, evaporator 6' and conduit 51 to continuous multi-stage distillation column 1 is positioned 50 cm above the bottom of distillation column 1. The operation for the production of DMC and EG was performed in substantially the same manner as in Example 3, except that the column bottom liquid of distillation column 1 was heated by means of reboiler 6 so as to maintain the weight ratio of DMC to MeOH in the column bottom liquid of distillation column 1 at 1/350; the reaction temperature of column bottom 8 was 56.0° C.; and gas density $\rho_g$ and gas velocity $u_g$ in distillation column 1 were 0.545 kg/m$^3$ and 0.393 m/s, respectively, and hence the F-factor of distillation column 1 was 0.29.

A column top condensate from column 1 (containing MeOH and DMC in concentrations of 65.3% by weight and 34.7% by weight, respectively) was obtained at a flow rate of 1,913.4 g/h.

A liquid reaction mixture (containing MeOH, DMC, EG and EC in concentrations of 48.2% by weight, 0.13% by weight, 49.9% by weight and 1.65% by weight, respectively) was withdrawn from column bottom 8 of distillation column 1 at a flow rate of 891.9 g/h and, as in Example 3, fed to low boiling point mixture-recovering column 10 which was operated under the same conditions as in Example 3. A part of a column top condensate from column 10 was returned in a liquid form to distillation column 1 at a position 50 cm above the bottom of distillation column 1 at a flow rate of 430.7 g/h. A part of a liquid withdrawn from column bottom 16 of column 10 was recovered from the production system through conduit 20 at a flow rate of 461.2 g/h. The withdrawn liquid (bottom liquid of column 10) contained EG, EC and by-produced diethylene glycol (DEG) in concentrations of 96.6% by weight, 3.2% by weight and 0.02% by weight, respectively. In the withdrawn liquid, 2-methoxyethanol (2ME) (as a possible by-product) was not detected.

From the above data, it can be seen that the conversion of EC was 97.6%, the yield of DMC was 97.6% (DMC was produced at a production rate of 611 g/h), the selectivity for DMC was not lower than 99.9%, the yield of EG was 97.6% (EG was produced at a production rate of 421.1 g/h), and the selectivity for EG was not lower than 99.9%. Also, the productivity of DMC in terms of the space time yield was: 572/2.26=253 g/liter·h. The conditions and results of the trans-esterification reaction are shown in Table 1.

EXAMPLE 7

Dimethyl carbonate (DMC) and ethylene glycol (EG) were continuously produced from ethylene carbonate (EC) and methanol (MeOH) by using substantially the same production system as in Example 1, except that continuous multi-stage distillation column 1 had a packing height of 85 cm. The operation for the production of DMC and EG was performed in substantially the same manner as in Example 1, except that the reaction conditions were as follows: a mixture of MeOH and DMC fed to distillation column 1 through conduit 5, evaporator 6' and conduit 5' had an [MeOH/DMC] weight ratio of 99.9/0.1 and was fed at a flow rate of 1,255 g/h; EC was fed at a flow rate of 528.1 g/h; a 9.6% by weight solution of sodium hydroxide (as a catalyst) in ethylene glycol was used (instead of a 4.8% by weight solution of potassium hydroxide); the reaction temperature of column bottom 8 of distillation column 1 was 49.8° C.; and gas density $\rho_g$ and gas velocity $u_g$ in distillation column 1 were 0.544 kg/m$^3$ and 0.285 m/s, respectively, and hence the F-factor of distillation column 1 was 0.21.

A column top condensate from column 1 (containing MeOH and DMC in concentrations of 63.3% by weight and 36.7% by weight, respectively) was obtained at a flow rate of 1,403.8 g/h.

A liquid reaction mixture (containing MeOH, DMC, EG and EC in concentrations of 70.0% by weight, 0.14% by weight, 27.8% by weight and 1.89% by weight, respectively) was withdrawn from column bottom 8 of distillation column 1 at a flow rate of 1,354.6 g/h and, as in Example 1, fed to low boiling point mixture-recovering column 10 which was operated under the same conditions as in Example 1. A part of a column top condensate from column 10 was returned in a liquid form to column bottom 8 of distillation column 1 at a flow rate of 949.8 g/h. A part of a liquid withdrawn from column bottom 16 of column 10 was recovered from the production system through conduit 20 at a flow rate of 404.8 g/h. The withdrawn liquid (bottom liquid of column 10) contained EG, EC and by-produced diethylene glycol (DEG) in concentrations of 93.1% by weight, 6.3% by weight and 0.02% by weight, respectively. In the withdrawn liquid, 2-methoxyethanol (2ME) (as a possible by-product) was not detected.

From the above data, it can be seen that the conversion of EC was 95.1%, the yield of DMC was 95.1% (DMC was produced at a production rate of 513.9 g/h), the selectivity for DMC was not lower than 99.9%, the yield of EG was 97.6% (EG was produced at a production rate of 354.1 g/h), and the selectivity for EG was not lower than 99.9%. Further, the productivity of DMC in terms of the space time yield was: 513.9/(1000×0.00225×0.85)=269 g/liter·h. The conditions and results of the transesterification reaction are shown in Table 1.

TABLE 1

| | Reaction Conditions | | | | Results | | | |
|---|---|---|---|---|---|---|---|---|
| | Pressure of column bottom[1] (Pa) | Temperature of column bottom[2] (° C.) | F-factor | MeOH/EC (Molar ratio) | Productivity of DMC in terms of the space time yield (g/liter · h) | Selectivity | | |
| | | | | | | DMC (%) | DEG (%) | 2ME (%) |
| Example 1 | 45,600 | 56.0 | 0.68 | 7.8 | 307 | >99.9 | 0.05 | 0 |
| Example 2 | 45,600 | 55.7 | 0.41 | 7.9 | 268 | >99.9 | 0.05 | 0 |

TABLE 1-continued

| | Reaction Conditions | | | | Results | | | |
|---|---|---|---|---|---|---|---|---|
| | Pressure of column bottom[*1] (Pa) | Temperature of column bottom[*2] (° C.) | F-factor | MeOH/EC (Molar ratio) | Productivity of DMC in terms of the space time yield (g/liter · h) | Selectivity | | |
| | | | | | | DMC (%) | DEG (%) | 2ME (%) |
| Comparative Example 1 | 101,000 | 79.6 | 0.29 | 7.9 | 202 | 99.3 | 0.60 | 0.02 |
| Comparative Example 2 | 101,000 | 76.7 | 0.41 | 11.5 | 234 | 99.4 | 0.60 | 0.02 |
| Example 3 | 45,600 | 56.2 | 0.29 | 7.6 | 253 | >99.9 | 0.05 | 0 |
| Comparative Example 3 | 45,600 | 55.9 | 0.12 | 3.1 | 108 | >99.9 | 0.05 | 0 |
| Example 4 | 30,400 | 47.1 | 0.94 | 7.0 | 371 | >99.9 | 0.02 | 0 |
| Example 5 | 30,400 | 47.0 | 0.60 | 7.3 | 328 | >99.9 | 0.02 | 0 |
| Example 6 | 45,600 | 56.0 | 0.29 | 7.6 | 270 | >99.9 | 0.02 | 0 |
| Example 7 | 45,600 | 49.8 | 0.21 | 6.8 | 269 | >99.9 | 0.02 | 0 |

Note:
[*1] the reaction pressure, as measured at the inner bottom of the multi-stage distillation column
[*2] the reaction temperature, as measured at the inner bottom of the multi-stage distillation column

REFERENCE EXAMPLE

Figure 2:
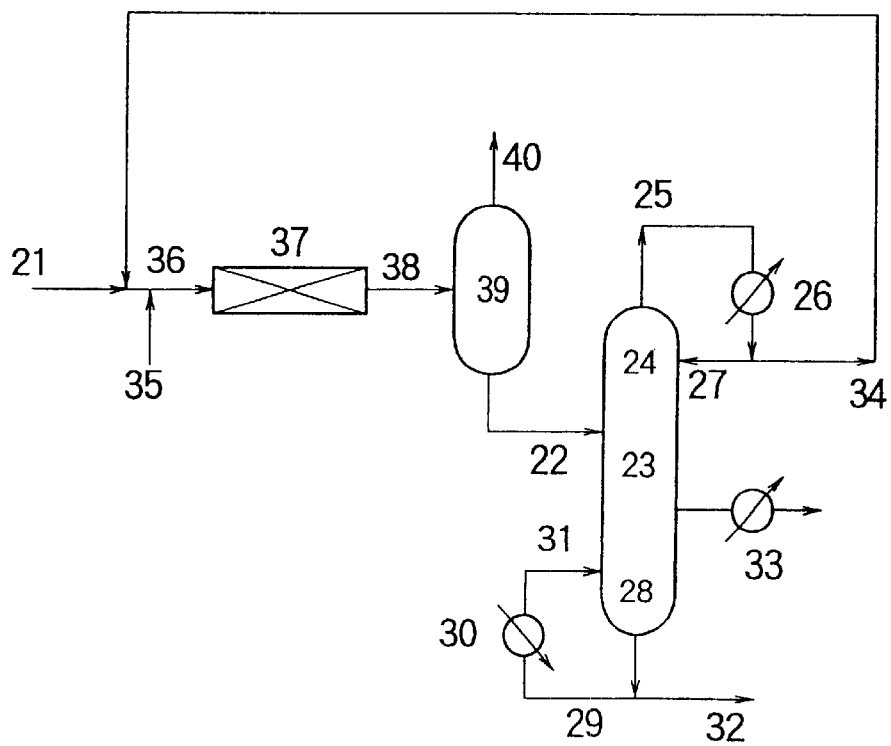
FIG. 2 is a diagram showing the system which was used for practicing Reference Example and Reference Comparative Example of the present application.

Using a production system as shown in FIG. 2, the liquid (containing unreacted EC) withdrawn from column bottom 16 of low boiling point mixture-recovering column 10 in Example 2 was subjected to hydrolysis with respect to the unreacted EC to thereby produce EG, and then subjected to distillation-separation, to thereby obtain a purified EG. Specifically, the operation was conducted as follows.

The liquid withdrawn from column bottom 16 of column 10 through conduit 20 at a flow rate of 547.3 g/h in Example 2 was introduced to continuous hydrolysis reactor 37 through conduit 21, together with water fed through conduit 35 at a flow rate of 5.7 g/h, to thereby effect a continuous hydrolysis reaction of EC in the liquid, wherein reactor 37 was comprised of a column having an inner diameter of 5 cm and a length of 100 cm and having packed therein Dixon packings (3 mmφ). The internal temperature and pressure of reactor 37 were maintained at 180° C. and $2.5 \times 10^6$ Pa (25 kg/cm$^2$-G), respectively. The weight ratio of water to EC at the inlet of reactor 37 was 0.5. The hydrolysis reaction mixture withdrawn from reactor 37 was introduced to gas-liquid separator 39 (which was operated under atmospheric pressure) through conduit 38. From separator 39, carbon dioxide was discharged through conduit 40 and a liquid containing EG was withdrawn through conduit 22. The withdrawn liquid containing EG was fed to diol-separating column 23 at a position 60 cm below the top of column 23, wherein column 23 was comprised of a column having been packed with Dixon packings (3 mmφ) and having an inner diameter of 5 cm and a packing height of 200 cm.

Diol-separating column 23 was operated under conditions wherein the pressure of column top 24 thereof was $2.7 \times 10^3$ Pa (20 torr). A gaseous mixture was withdrawn from column top 24 of column 23 and condensed by condenser 26 to obtain a condensate (hereinafter referred to simply as "column top condensate from column 23"), a part of which was refluxed to column 23 through conduit 27 (reflux ratio: 5), while returning the remainder of the condensate to continuous hydrolysis reactor 37 through conduit 34 at a flow rate of 16.4 g/h. A liquid withdrawn from the bottom of column 23 was heated by reboiler 30 and returned to column 23 through conduit 31. The temperature of column bottom 28 of column 23 was 116° C. A gaseous mixture was withdrawn from the withdrawal port provided in the side wall of column 23 at a position 120 cm below the top of column 23 at a flow rate of 528.8 g/h, and condensed by condenser 33, to thereby obtain EG as a side cut (side stream) [EG content was not lower than 99.99% by weight and none of EC, DEG and 2ME was detected]. A part of the liquid withdrawn from column bottom 28 of column 23 was recovered from the production system through conduit 32 at a flow rate of 10.5 g/h. The withdrawn liquid (bottom liquid of column 23) contained EG and DEG in concentrations of 81.5% by weight and 1.3% by weight, respectively.

REFERENCE COMPARATIVE EXAMPLE

Production of a purified EG was conducted in substantially the same manner as in Reference Example, except that the liquid withdrawn from column bottom 16 of low boiling point mixture-recovering column 10 in Comparative Example 1 was used instead of the liquid withdrawn in Example 2 and that the operation was slightly modified as described below.

That is, the liquid withdrawn from column bottom 16 of column 10 through conduit 20 at a flow rate of 547.3 g/h in Comparative Example 1 was introduced to continuous hydrolysis reactor 37, together with water fed through conduit 35 at a flow rate of 41.1 g/h. A part of a column top condensate from diol-separating column 23 was returned to continuous hydrolysis reactor 37 through conduit 34 at a flow rate of 119.5 g/h.

The temperature of column bottom 28 of diol-separating column 23 was 116° C. (which was the same as in Reference Example). When diol-separating column 23 was operated under conditions wherein the reflux ratio of the column top condensate from column 23 and the flow rate of the liquid withdrawn from column bottom 28 of column 23 through conduit 32 were the same as in Reference Example, 500 ppm of DEG was detected in a side cut (side stream) from column 23. In order to lower the amount of DEG in the side stream from column 23, the reflux ratio of the column top condensate from column 23 was raised to 8 and the flow rate of the liquid withdrawn from column bottom 28 of column 23 through conduit 32 (containing EG and DEG in concentrations of 94.6% by weight and 2.8% by weight, respectively) was increased to 67.2 g/h. As a result, the flow rate of the side stream from column 23 became 475.6 g/h. In addition to EG (contained in a concentration of 99.98% by weight), the side stream contained DEG and 2ME in concentrations of 0.005% by weight and 0.019% by weight, respectively.

As mentioned above, in Reference Comparative Example, use is made of the liquid withdrawn from column bottom 16 of low boiling point mixture-recovering column 10 of the production system used in Comparative Example 1 (the liquid containing DEG and 2ME in large amounts). As a result, purified EG obtained in Reference Comparative Example as a side stream from diol-separating column 23 contains impurities, such as DEG and 2ME. Whereas, in Reference Example [using a liquid withdrawn from column bottom 16 of column 10 of the production system used in Example 2 (the liquid containing only a small amount of DEG and no 2ME)], neither DEG nor 2ME was detected in a side stream from diol-separating column 23. Also, the flow rate (67.2 g/h) of a liquid withdrawn (as a waste) from column bottom 28 of diol-separating column 23 in Reference Comparative Example is much higher than that (10.5 g/h) in Reference Example [i.e., 67.2/10.5=6.4 (times)].

INDUSTRIAL APPLICABILITY

By the method of the present invention, continuous production of a dialkyl carbonate and a diol from a cyclic carbonate and an aliphatic monohydric alcohol can be easily performed with high productivity and high selectivity (i.e., a lowering of the occurrence of by-products), without using complicated equipment. Therefore, the method of the present invention is extremely advantageous from the commercial viewpoint.

What is claimed is:

1. A method for continuously producing a dialkyl carbonate and a diol from a cyclic carbonate and an aliphatic monohydric alcohol, comprising continuously feeding a cyclic carbonate represented by the following formula (A):

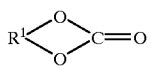

(A)

wherein $R^1$ is a divalent group represented by the formula —$(CH_2)_m$—, wherein m is an integer of from 2 to 6, which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

$R^2OH$ (B)

wherein $R^2$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group, to a continuous multi-stage distillation column, and continuously effecting a transesterification between said cyclic carbonate and said aliphatic monohydric alcohol in the presence of a transesterification catalyst in said multi-stage distillation column, thereby continuously producing a dialkyl carbonate and a diol, while continuously withdrawing a low boiling point mixture containing the produced dialkyl carbonate in a gaseous form from an upper portion of said multi-stage distillation column and continuously withdrawing a high boiling point mixture containing the produced diol in a liquid form from a lower portion of said multi-stage distillation column, wherein said transesterification is performed under conditions wherein:
(a) the reaction pressure is $5 \times 10^4$ Pa or less, as measured at the inner bottom of said multi-stage distillation column,
(b) the reaction temperature is in the range of from −20° C. to less than 60° C., as measured at the inner bottom of said multi-stage distillation column, and
(c) said multi-stage distillation column has an F-factor in the range of from 0.2 to 5.0, said F-factor being represented by the following formula (1):

$$F\text{-factor} = u_g (\rho_g)^{1/2} \qquad (1)$$

wherein $u_g$ represents the gas velocity (m/s) in the multi-stage distillation column and $\rho_g$ represents the gas density (kg/m³) in the multi-stage distillation column.

2. The method according to claim 1, wherein said F-factor is in the range of from 0.4 to 4.0.

3. The method according to claim 2, wherein said F-factor is in the range of from 0.6 to 4.0.

4. The method according to any one of claims 1 to 3, wherein said aliphatic monohydric alcohol contains a concomitant dialkyl carbonate in an amount of from 0 to 40% by weight, based on the total weight of said aliphatic monohydric alcohol and said concomitant dialkyl carbonate.

5. The method according to any one of claims 1 to 3, wherein said cyclic carbonate is at least one carbonate selected from the group consisting of ethylene carbonate and propylene carbonate, and said aliphatic monohydric alcohol is methanol.

6. The method according to any one of claims 1 to 3, wherein:

said cyclic carbonate is continuously fed, to an upper portion of said continuous multi-stage distillation column, in a liquid form or a gas-liquid mixture form, and said aliphatic monohydric alcohol is continuously fed, to a lower portion of said continuous multi-stage distillation column, in a gaseous form or a gas-liquid mixture form, or in a gaseous form and in a liquid form individually.

* * * * *